United States Patent [19]

Muramatsu et al.

[11] 4,433,152
[45] Feb. 21, 1984

[54] AMIDINOPIPERIDINE DERIVATIVES

[75] Inventors: Mutsumi Muramatsu; Toshio Satoh, both of Tokushima; Hiroyasu Sekine, Kisai; Atsushi Tendo; Yoshio Kikawa, both of Misato; Kaname Kondo, Koshigaya, all of Japan

[73] Assignee: Nippon Chemiphar Co., Ltd., Tokyo, Japan

[21] Appl. No.: 379,714

[22] Filed: May 19, 1982

[30] Foreign Application Priority Data

May 25, 1981 [JP]  Japan .................................. 56-78142
May 25, 1981 [JP]  Japan .................................. 56-78143
Aug. 22, 1981 [JP]  Japan .................................. 56-130856

[51] Int. Cl.$^3$ .......................................... C07D 401/12
[52] U.S. Cl. ................................. 546/193; 546/206; 546/227; 546/231; 546/246; 546/248
[58] Field of Search .............. 546/246, 231, 206, 193, 546/227

[56] References Cited

U.S. PATENT DOCUMENTS 3,189,601  6/1965  Mull .................................. 546/246 X
3,979,398  9/1976  White .............................. 548/342 X

OTHER PUBLICATIONS

March, J., *Advanced Organic Chemistry*, McGraw Hill, NY, 1968, pp. 319-322.

McOmie, J., (Editor), *Protective Groups in Organic Chemistry*, Plenum Press, London, 1973, pp. 196-199.

*Primary Examiner*—Richard A. Schwartz
*Attorney, Agent, or Firm*—Oblon, Fisher, Spivak, McClelland & Maier

[57] ABSTRACT

A compound of the formula,

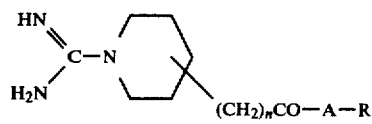

wherein R represents a hydrogen atom, a naphthyl, indanyl, tetrahydronaphthyl or pyridyl group, or a phenyl group which may have 1 to 3 substituents selected from the group consisting of a halogen atom, and an alkyl, alkenyl, alkoxy, alkanoyl, cyano, formyl, trifluoromethyl, phenyl, phenylalkyl, alkanoyl-amino, aminosulfonyl, carboxyl, alkoxycarbonyl, benzyloxycarbonyl, benzoylvinyl, phenylvinylcarbonyl, carboxyvinyl, and diphenyl-methyloxycarobnylvinyl group, A represents an oxygen or sulfur atom, and n represents an integer of 0 to 3, with the proviso that when n is an integer of 0, R must not be a hydrogen atom, or a pharmaceutically acceptable salt thereof is effectively useful for inhibiting a complement reaction, inflammation caused by an allergic reaction, and platelet aggregation.

3 Claims, No Drawings

AMIDINOPIPERIDINE DERIVATIVES

BACKGROUND OF THE INVENTION

1. Field of the Invention

This invenion relates to novel amidinopiperidine derivatives and a process for producing such derivatives.

2. Description of the Prior Art

Hamanaka and Frnest, S. have reported that 1-amidino-3-piperidinecarboxylic acid and 1-amidino-4-piperidinecarboxylic acid are useful as materials for synthetic penicillins (U.S. Pat. Nos. 3,870,709, 3,933,797 and 3,972,872). However, no research has been made of the pharmacological action of 1-amidino-3-piperidinecarboxylic acid.

A variety of amidinopiperidine derivatives have been studied, resulting in the present discovery.

SUMMARY OF THE INVENTION

Accordingly, one object of the present invention is to provide novel amidinopiperidine derivatives which exhibit strong inhibitory effects on a complement reaction, inflammation caused by an allergic reaction, and platelet aggregation.

It is another object of the invention to provide a process for producing these amidinopiperidine derivatives.

These and other objects of the invention as hereinafter will become more readily apparent can be attained by the provision of compounds of the formula (I) and pharmaceutically acceptable salts thereof,

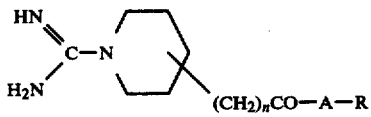

(I)

wherein R represents a hydrogen atom, a naphthyl, indanyl, tetrahydronaphthyl or pyridyl group, or a phenyl group which may have 1 to 3 substituents selected from the group consisting of a hydrogen atom, and an alkyl, alkenyl, alkoxy, alkanoyl, cyano, formyl, trifluoromethyl, phenyl, phenylalkyl, alkanoylamino, aminosulfonyl, carboxyl, alkoxycarbonyl, benzyloxycarbonyl, benzoylvinyl, phenylvinylcarboxyl, carboxyvinyl, and diphenylmethyloxycarbonylvinyl group, A represents an oxygen or sulfur atom, and n represents an integer of 0 to 3, with the proviso that when n is an integer of 0, R must not be a hydrogen atom. The compounds of the formula (I) have been found to possess excellent inhibitory effects on a complement reaction, inflammation caused by an allergic reaction, and platelet aggregation.

Particularly, compounds of the formula (Ia) and pharmaceutically acceptable salts thereof,

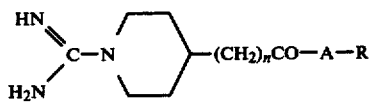

(Ia)

wherein R is the same as defined above, are substantially excellent in their pharmacological action just discussed.

DETAILED DESCRIPTION OF THE PREFERRED EMBODIMENTS

R in the formula (I) may be a hydrogen atom, a naphthyl, indanyl, tetrahydronaphthyl or pyridyl group, or a phenyl group which may have 1 to 3 substituents selected from the group consisting of a halogen atom, and an alkyl, alkenyl, alkoxy, alkanoyl, cyano, cyclohexyl, formyl, trifluoromethyl, phenyl, phenylalkyl, acetamino, sulfonylamino, carboxyl, alkoxycarbonyl, benzyloxycarbonyl, benzoylvinyl, phenylvinylcarbonyl, carboxyvinyl, and diphenylmethyloxycarbonylvinyl group. Suitable examples of the phenyl group for R include phenyl, p-methylphenyl, o-methylphenyl, 2,4-dimethylphenyl, 2,6-dimethylphenyl, 2,4,6-trimethylphenyl, p-isopropylphenyl, p-t-butylphenyl, p-cyclohexylphenyl, p-chlorophenyl, p-fluorophenyl, p-bromophenyl, 2,4-dichlorophenyl, 2-chloro-4-t-butylphenyl, p-methoxyphenyl, o-ethoxyphenyl, p-propoxyphenyl, o-allylphenyl, 4-allyl-2-methoxyphenyl, p-acetylphenyl, p-propanoylphenyl, o-propanoylphenyl, p-cyanophenyl, o-cyanophenyl, p-formylphenyl, o-formylphenyl, m-trifluoromethylphenyl, p-phenylphenyl, o-phenylphenyl, p-aminosulfonylphenyl, o-aminosulfonylphenyl, p-acetaminophenyl, o-acetaminophenyl, 4-formyl-2-methoxyphenyl, p-benzylphenyl, p-(α,α-dimethylbenzyl)phenyl, p-carboxyphenyl, p-methoxycarbonylphenyl, o-benzyloxycarbonylphenyl, o-carboxyphenyl, cinnamoylphenyl, o-(β-phenylcarbonylethenyl)phenyl, p-(β-diphenylmethyloxycarbonyl)ethenylphenyl, p-(β-carboxy)ethenylphenyl, 3-methoxy-4-(β-carboxyethenyl)phenyl group and the like. Other suitable groups for R include 1-naphthyl, 2-naphthyl, 5-indanyl, 5,6,7,8-tetrahydro-2-naphthyl, 3-pyridyl group and the like.

A in the formula (I) may be an oxygen or sulfur atom, and n is an integer of 0 to 3. However, when n is an integer of 0, R must not be a hydrogen atom.

Pharmaceutically acceptable salts of the compounds of the present invention are acid salts derived from hydrochloric acid, sulfuric acid, phosphoric acid, hydrobromic acid, acetic acid, lactic acid, maleic acid, fumaric acid, tartaric acid, citric acid, methanesulfonic acid, p-toluenesulfonic acid and the like.

According to the invention, compounds of the formula (II),

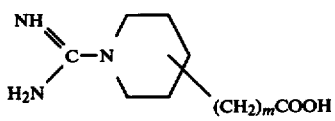

(II)

wherein m is an integer of 1 to 3, are produced by reacting compounds of the formula (III),

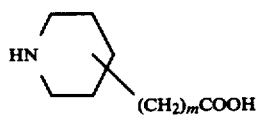

(III)

wherein m is the same as defined above, with an alkyl isourea or alkyl isothiourea, or a salt thereof.

This reaction is carried out with stirring at room temperature for 5 to 20 hours in the presence of sodium hydroxide, potassium hydroxide, sodium hydrogen carbonate or the like. The compounds of the formula (III) are produced by hydrogenation of the corresponding pyridylcarboxylic acid or pyridylfatty acid in the presence of a catalyst such as platinum.

Compounds of the formula (Ib) and pharmaceutically acceptable salts thereof,

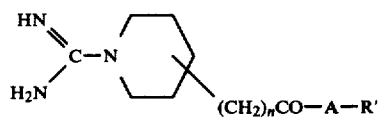
(Ib)

wherein R′ is a naphthyl, indanyl, tetrahydronaphthyl or pyridyl group, or a phenyl group which may have 1 to 3 substituents selected from the group consisting of a halogen atom, and an alkyl, alkenyl, alkoxy, alkanoyl, cyano, formyl, trifluoromethyl, phenyl, phenylalkyl, alkanoylamino, aminosulfonyl, carboxyl, alkoxycarbonyl, benzyloxycarbonyl, benzoylvinyl, phenylvinylcarbonyl, and diphenylmethyloxycarbonylvinyl group, and A and n are the same as defined above, are produced by reacting compounds of the formula (IV),

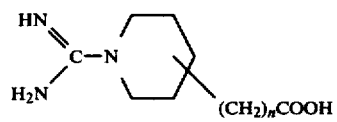
(IV)

wherein n is the same as defined above, or reactive derivatives thereof with compounds of the formula (V),

R′—A—H (V)

wherein R′ and A are the same as defined above, or sulfite derivatives thereof.

Suitable reactive derivatives of the compounds of the formula (IV) include acid halides such as acid chloride, acid bromide and the like, and mixed anhydrides of ethylchloroformate. Suitable sulfite derivatives of the compounds of the formula (V) include diarylsulfite derivatives such as diphenylsulfite, bis-(p-chlorophenyl)sulfite and the like.

The reaction of the compounds of the formula (IV) with the compunds of the formula (V) is carried out with stirring at room temperature for 1 to 20 hours. Suitable solvents which may be used include dimethylformamide, dimethylacetamide, pyridine and the like.

The reaction of the reactive derivatives of the compounds of the formula (IV) with the compounds of the formula (V) is effected with stirring at a temperature of room temperature to the boiling point of the solvent. Suitable solvents which may be used include dimethylformamide, dimethylacetamide, pyridine, dichloromethane, dichloroethane, chloroform, acetonitrile and the like. In such instance, it is sometimes recommended to use an acid-binding agent such for example as triethylamine, dimethylaniline or pyridine.

When the compounds of the formula (IV) are reacted directly without conversion to any reactive intermediates thereof, the reaction is preferably carried out in the presence of a condensing agent, for example, carbodiimide such as dicyclohexylcarbodiimide, or a Lewis acid such as phosphorousoxychloride or borontrifluoride. The reaction is accomplished using a solvent such for example as toluene, xylene or dimethylformamide, a solvent mentioned above, or a mixture thereof at a temperature of room temperature to the boiling point of the solvent.

Of the compounds of the formula (I), when a compound having a carboxyphenyl or carboxyvinylphenyl group is desired, a compound obtained as having a benzyloxycarbonylphenyl or diphenylmethyloxycarbonylvinylphenyl group may be hydrogenated in the presence of a catalyst such as palladium-carbon. Further, suitable acid salts of the compounds of the formula (I) can be isolated from the reaction mixture by the known method.

The thus obtained compounds of the formula (I) have some excellent pharmacological activities. Such compounds are substantially effective to inhibit a complement reaction. The compounds also exert marked effects on the inhibition of inflammation caused by an allergic reaction, i.e. the inhibition of the Arthus reaction and delayed type hypersensitivity. Moreover, the compounds are effectively useful as an inhibitor of platelet aggregation.

1. Inhibition of Hemolysis by Complement (1) Inhibition of Hemolysis by Classical Pathway of Complement A mixture of fresh human (or guinea pig) plasma and a test sample solution was incubated at 37° C. for 30 minutes, and the mixture was then cooled to 4° C. To the mixture were added a gelatin-veronal buffer and then an EA (seep erythrocytes-anti-sheep erythrocytes) suspension, and the resulting mixture was incubated at 37° C. for 90 minutes. The mixture was centrifuged at 4° C. for 5 minutes (2,500 rpm), and the supernatant was determined from the absorbance at 541 nm.

The inhibitory effects are shown in Table 1 as the 50 percent inhibition concentration [CH50(mM)].

(2) Inhibition of Hemolysis by Alternative Pathway of Complement

A mixture of fresh human (or guinea pig) plasma and a test sample solution was incubated at 37° C. for 30 minutes. To the mixture was added a rabbit erythrocytes suspension, and the resulting mixture was incubated at 37° C. for 40 minutes. EDTA was added to the mixture. The resulting mixture was centrifuged for 5 minutes (2,500 rpm), and the supernatant was determined from the absorbance at 413 nm.

The inhibitory effects are shown in Table 1 as the 50 percent inhibition concentration [ACH50(mM)].

TABLE 1

| Test Compound | Inhibition of Homolysis by Complement | |
|---|---|---|
| | CH50 (mM) | ACH50 (mM) |
| 1 | 0.44 | 0.40 |
| 2 | 0.44 | 0.28 |
| 3 | 0.57 | 0.19 |
| 4 | 0.17 | 0.25 |
| 5 | 0.23 | 0.18 |
| 6 | 0.20 | <0.10 |
| 7 | 1< | <0.10 |
| 8 | 1< | 0.31 |
| 9 | 1< | 0.30 |
| 10 | 0.67 | 0.26 |
| 11 | 1< | 0.30 |
| 12 | 0.20 | 0.21 |
| 13 | 1< | 0.17 |
| 14 | 0.27 | 0.34 |
| 15 | 0.32 | 0.32 |
| 16 | 1< | 0.30 |
| 17 | 0.86 | 0.08 |
| 18 | 1< | 0.26 |

TABLE 1-continued

Inhibition of Homolysis by Complement

| Test Compound | CH50 (mM) | ACH50 (mM) |
|---|---|---|

Compound 1: Phenyl 1-amidino-4-piperidinecarboxylate hydrochloride
2: p-Methylphenyl 1-amidino-4-piperidinecarboxylate hydrochlorlde
3: p-Methoxyphenyl 1-amidino-4-piperidinecarboxylate hydrochloride
4: p-Chlorophenyl 1-amidino-4-piperidinecarboxylate hydrochloride
5: 2,4-Dichlorophenyl 1-amidino-4-piperidinecarboxylate hydrochloride
6: p-t-Butylphenyl 1-amidino-4-piperidinecarboxylate hydrochloride
7: Phenyl 1-amidino-4-piperidinepropionate hydrochloride
8: p-Methoxyphenyl 1-amidino-4-piperidinepropionate hydrochloride
9: p-Chlorophenyl 1-amidino-4-piperidinepropionate hydrochloride
10: 2,4-Dichlorophenyl 1-amidino-4-piperidinepropionate hydrochloride
11: 2-Chloro-4-t-butylphenyl 1-amidino-4-piperidinepropionate hydrochloride
12: p-Acetylphenyl 1-amidino-4-piperidinepropionate hydrochloride
13: p-Acetaminophenyl 1-amidino-4-piperidinepropionate hydrochloride
14: 1-Naphthyl 1-amidino-4-piperidinepropionate hydrochloride
15: 2-Naphthyl 1-amidino-4-piperidinepropionate hydrochloride
16: p-Fluorophenyl 1-amidino-4-piperidinepropionate hydrochloride
17: p-Aminosulfonylphenyl 1-amidino-4-piperdidinepropionate hydrochloride
18: 3-Pyridyl 1-amidino-4-piperidinepropionate hydrochloride

2. Inhibition of Edema by Allergic Reaction

(1) Inhibition of Edema by Reverse Arthus Reaction in Guinea Pigs

Egg albumin with saline (20 mg/ml/kg) was intravenously injected into the fore limb of a guinea pig. 15 minutes later, 0.05 ml of rabbit anti-egg albumin serum was subcutaneously injected into the back of the guinea pig. 3 hours later, the reddening and edema area (mm$^2$) was measured. Test samples were administered per os 1 hour prior to the antigen injection.

The results obtained are shown in Table 2 as the inhibition percent.

TABLE 2

Inhibitory Effects on Reverse Arthus Reaction

| Test Compound | Dose (mg/kg, P.O.) | Inhibition (%) |
|---|---|---|
| 6 | 500 | 90.08 |
| 12 | 50 | 49.97 |
| 15 | 50 | 67.26 |
| 17 | 50 | 47.64 |
| 18 | 50 | 63.75 |
| 19 | 50 | 50.16 |
| 20 | 50 | 63.56 |
| 21 | 50 | 55.07 |
| 22 | 50 | 53.18 |
| 23 | 50 | 41.60 |
| 24 | 50 | 71.52 |
| 25 | 50 | 50.53 |
| 26 | 50 | 67.72 |
| 27 | 50 | 59.41 |
| 28 | 50 | 57.65 |
| 29 | 50 | 49.97 |
| 30 | 50 | 55.70 |
| 31 | 50 | 73.20 |

Compounds 6, 12, 15, 17 and 18: Same as defined in

TABLE 2-continued

Inhibitory Effects on Reverse Arthus Reaction

| Test Compound | Dose (mg/kg, P.O.) | Inhibition (%) |
|---|---|---|

Table 1

Compound 19: p-Isopropylphenyl 1-amidino-4-piperidinepropionate hydrochloride
20: o-Allylphenyl 1-amidino-4-piperidinepropionate hydrochloride
21: p-t-Butylphenyl 1-amidino-4-piperidinepropionate hydrochloride
22: p-(α,α-Dimethylbenzyl)phenyl 1-amidino-4-piperidinepropionate hydrochloride
23: p-Fluorophenyl 1-amidino-4-piperidinepropionate hydrochloride
24: p-Formylphenyl 1-amidino-4-piperidinepropionate hydrochloride
25: p-Phenylphenyl 1-amidino-4-piperidinepropionate hydrochloride
26: o-Methylphenyl 1-amidino-4-piperidinepropionate hydrochloride
27: o-Cyanophenyl 1-amidino-4-piperidinepropionate hydrochloride
28: o-Phenylphenyl 1-amidino-4-piperidinepropionate hydrochloride
29: m-Trifluoromethylphenyl 1-amidino-4-piperidinepropionate hydrochloride
30: 4-Formyl-2-methoxylphenyl 1-amidino-4-piperidinepropionate hydrochloride
31: 5,6,7,8-Tetrahydro-2-naphthyl 1-amidino-4-piperidinepropionate hydrochloride

(2) Inhibition of Edema by Delayed Type Hypersensitivity in MIce

ICR strain female mice were sensitized with BCG (1 mg/animal) with saline (subcutaneously injected into the back of each mouse). After the lapse of 6 days, the thickness of the foot was measured, and each animal was sensitized once more with BCG (1 mg/animal) with saline (subcutaneously injected into the hind paw). The thickness of the foot injected was measured again. Test samples were administered per os daily for 6 days from the sensitization.

The results obtained are shown in Table 3 as the inhibition percent.

TABLE 3

Inhibitory Effects on Delayed Type Hypersensitivity

| Test Compound | Dose (mg/kg/day, P.O.) | Inhibition (%) |
|---|---|---|
| 6 | 10 | 54.75 |
| " | 5 | 30.77 |
| 20 | 10 | 62.67 |
| 21 | 10 | 55.20 |
| " | 5 | 50.23 |
| 22 | 10 | 43.56 |
| 31 | 10 | 60.61 |
| 32 | 10 | 54.69 |
| 33 | 10 | 39.18 |
| 34 | 10 | 48.98 |
| 35 | 10 | 52.24 |
| 36 | 10 | 45.25 |
| " | 5 | 33.03 |

Compounds 6, 20, 21, 22 and 31: Same as defined in Tables 1 and 2

Compound 32: 2,4-Dimethylphenyl 1-amidino-4-piperidinecarboxylate hydrochloride
33: p-Cyclohexylphenyl 1-amidino-4-piperidinecarboxylate hydrochloride
34: o-Carboxyphenyl 1-amidino-4-piperidinepropionate hydrochloride
35: 5-Indanyl 1-amidino-4-piperidinepropionate hydrochloride
36: Phenyl 1-amidino-4-piperidineacetate

TABLE 3-continued

| Inhibitory Effects on Delayed Type Hypersensitivity | | |
|---|---|---|
| Test Compound | Dose (mg/kg/day, P.O.) | Inhibition (%) |
| hydrochloride | | |

As stated above, the present compounds exhibit excellent inhibitory effects on platelet aggregation. For example, 2',4'-dimethylphenyl 1-amidino-4-piperidinepropionate hydrochloride and 4'-allyl-2'-methoxyphenyl 1-amidino-4-piperidinepropionate hydrochloride completely blocked arachidonic acid-induced and collagen-induced platelet aggregation in vitro with use of rabbit platelet-rich plasma at a concentration of 5 µg/ml.

The above disclosure generally describes the present invention. A more complete understanding will be obtained by the following specific examples which are presented herein for purposes of illustration only and are not construed as limiting to the invention.

EXAMPLE 1

1-Amidino-4-piperidinepropionic acid 20 ml of 2 N sodium hydroxide was stirred with ice-cooling, and 3.4 g of o-methylisourea sulfate and 3.1 g of piperidine-4-propionic acid were added to the aqueous sodium hydroxide solution. To the mixture was then added 5 ml of water, and the resulting mixture was stirred at room temperature for 19 hours. The product precipitated was separated by filtration and washed with a small amount of cold water three times, then with acetone and finally with ether to obtain 2.0 g of 1-amidino-4-piperidinepropionic acid as colorless crystals having a melting point of 294° C. (decomposed).

EXAMPLE 2

1-Amidino-4-piperidinepropionic acid hydrochloride 2.0 g of 1-amidino-4-piperidinepropionic acid prepared in Example 1 was dissolved in 15 ml of 1 N hydrochloric acid. To the solution was added 0.2 g of activated charcoal, and the resulting mixture was stirred for 30 minutes. After removal of activated charcoal by filtration, the filtrate was concentrated under reduced pressure. Acetone was added to the residue to give crystals which were then washed with acetone and further with ether and dried to obtain 1.7 g of 1-amidino-4-piperidinepropionic acid hydrochloride as prisms having a melting point of 199.5° to 202° C.

The thus obtained prisms were further purified to give crystals having a melting point of 203° to 204° C.

IR $\nu_{max}^{KBr}$ cm$^{-1}$: 1710 (C=O).

EXAMPLE 3

Phenyl 1-amidino-4-piperidinepropionate hydrochloride

A mixture of 707 mg of 1-amidino-4-piperidinepropionic acid hydrochloride and 1.1 g of diphenyl sulfite was stirred overnight at room temperature in a solution of 8 ml of dry dimethylformamide and 3 ml of dry pyridine. The solvent was removed under reduced pressure, and the residue was washed twice with 20 ml of ether to give crystals. The crystals were washed with acetone and dissolved in 4 ml of methanol. The resulting solution was added to a solution of 20 ml of ether and 30 ml of acetone to give crystals. The crystals were washed twice with hot ethyl acetate to obtain 643 mg (yield: 69%) of phenyl 1-amidino-4-piperidinepropionate hydrochloride as colorless crystals having a melting point of 167° to 170.5° C.

IR $\nu_{max}^{KBr}$ cm$^{-1}$: 1735 (C=O).

NMR(CD$_3$OD)δ: 1.00–4.00 (13H, m, piperidine protons and C$\underline{H}_2$C$\underline{H}_2$CO); 6.90–7.40 (5H, m, aromatic protons).

EXAMPLE 4 o-Benzyloxycarbonylphenyl 1-amidino-4-piperidinepropionate hydrochloride

A mixture of 707 mg of 1-amidino-4-piperidinepropionic acid hydrochloride and 2.3 g of bis-(o-benzyloxycarbonylphenyl)sulfite was stirred overnight at room temperature in a solution of 8 ml of dry dimethylformamide and 3 ml of dry pyridine. The solvent was removed under reduced pressure, and the residue was washed with 20 ml of ether three times and then with 20 ml of ethyl acetate to give crystals. The crystals were recrystallized from isopropanol to obtain 710 mg (yield: 51%) of o-benzyloxycarbonyl 1-amidino-4-piperidinepropionate hydrochloride as colorless crystals having a melting point of 148° to 150° C.

IR $\nu_{max}^{KBr}$ cm$^{-1}$: 1750, 1705 (C=O).

NMR(CD$_3$OD)δ: 1.00–4.00 (13H, m, piperidine protons C$\underline{H}_2$C$\underline{H}_2$CO); 5.20 (2H, s, C$\underline{H}_2$—Ph); 6.96–8.96 (9H, m, aromatic protons).

EXAMPLE 5 o-Hydroxycarbonylphenyl 1-amidino-4-piperidinepropionate hydrochloride 5.5 g of o-benzyloxycarbonylphenyl 1-amidino-4-piperidinepropionate hydrochloride was dissolved in a solution of 60 ml of t-butyl alcohol and 60 ml of water. 225 mg of 10% paradium-carbon was added to the solution, and the mixture was stirred at room temperature for 1 hour in the presence of hydrogen (starting pressure: 2.4 kg/cm$^2$). The catalyst was removed by filtration, and the solvent was removed. The residue was washed with t-butyl alcohol to obtain 3.5 g (yield: 79.7%) of o-hydroxycarbonylphenyl 1-amidino-4-piperidinepropionate hydrochloride as colorless needles having a melting point of 192° to 194° C.

IR $\nu_{max}^{KBr}$ cm$^{-1}$: 1745, 1725 (C=O).

NMR(DMSO-d$_6$)δ: 0.8–2.0 (7H, m, 3- and 5-H$_2$, 4-H, β-H$_2$); 2.65 (2H, distorted t, α-H$_2$); 2.8–4.2 (4H, m, 2- and 6-H$_2$); 7.2–8.3 (4H, m, aromatic protons).

EXAMPLE 6

2',4'-Dichlorophenyl 1-amidino-4-piperidinepropionate hydrochloride

A mixture of 1.7 g of 1-amidino-4-piperidinepropionic acid hydrochloride and 4.0 g bis-(2,4-dichlorophenyl)sulfite was stirred at room temperature for 45 minutes in a solution of 10 ml of dry dimethylformamide and 3 ml of dry pyridine. The solvent was removed under reduced pressure, and 30 ml of ethyl acetate was added to the residue. The mixture was then stimulated to give crystals. The crystals were washed with ethyl acetate and then with ether to obtain 2.0 g (yield: 73%) of 2',4'-dichlorophenyl 1-amidino-4-piperidinepropionate hydrochloride as colorless powder having a melting point of 152° to 156° C.

IR $\nu_{max}^{KBr}$ cm$^{-1}$: 1760 (C=O).

NMR(CD$_3$OD)δ: 1.10–4.00 (13H, m, piperidine protons and C$\underline{H}_2$C$\underline{H}_2$CO); 7.20–7.70 (3H, m, aromatic protons).

EXAMPLE 7 p-Chlorophenyl 1-amidino-4-piperidinepropionate hydrochloride

A mixture of 1.5 g of 1-amidino-4-piperidinepropionic acid hydrochloride and 7.7 g of bis-(p-chlorophenyl)sulfite was stirred at room temperature for 30 minutes in a solution of 12 ml of dry dimethylformamide and 6 ml of dry pyridine. The solvent was removed under reduced pressure, and ether was added to the residue to give crystals. The crystals were washed with ether twice and then with ethyl acetate and recrystallized from methanol-ether to obtain 1.75 g (yield: 79.5%) of p-chlorophenyl 1-amidino-4-piperidinepropionate hydrochloride as colorless crystals having a melting point of 173° to 176° C.

IR $\nu_{max}^{KBr}$ cm$^{-1}$: 1753 (C=O).

NMR(CD$_3$OD)δ: 1.08–4.05 (13H, m, piperidine protons and C$\underline{H}_2$C$\underline{H}_2$CO); 7.15–7.67 (4H, m, aromatic protons).

EXAMPLE 8 p-Methylphenyl 1-amidino-4-piperidinepropionate hydrochloride

A mixture of 1.5 g of 1-amidino-4-piperidinepropionic acid hydrochloride and 6.7 g of bis-(p-methylphenyl)sulfite was stirred at room temperature for 2 hours in a solution of 12 ml of dry dimethylformamide and 6 ml of dry pyridine. The solvent was removed under reduced pressure, and ether was added to the residue to give crystals. The crystals were washed with ether twice and then with ethyl acetate and recrystallized from isopropyl alcohol-isopropyl ether to obtain 1.87 g (yield: 90%) of p-methylphenyl 1-amidino-4-piperidinepropionate hydrochloride as colorless crystals having a melting point of 182° to 184° C.

IR $\nu_{max}^{KBr}$ cm$^{-1}$: 1743 (C=O).

NMR (CD$_3$OD)δ: 1.00–4.00 (13H, m, piperidine protons and C$\underline{H}_2$C$\underline{H}_2$CO) 2.29 (3H, s, —C$\underline{H}_3$), 6.61–7.20 (4H, m, aromatic protons).

EXAMPLE 9 p-Methoxyphenyl 1-amidino-4-piperidinepropionate hydrochloride

A mixture of 1.5 g of 1-amidino-4-piperidinepropionic acid hydrochloride and 6.8 g of bis-(p-methoxyphenyl)sulfite was stirred at room temperature for 35 hours in a solution of 14 ml of dry dimethylformamide and 7 ml of dry pyridine. The solvent was removed under reduced pressure, and ether was added to the residue to give crystals. The crystals were washed with ether twice and then with ethyl acetate and recrystallized from isopropyl alcohol-isopropyl ether to obtain 1.25 g (yield: 57%) of p-methoxyphenyl 1-amidino-4-piperidinepropionate hydrochloride as colorless crystals having a melting point of 148° to 151° C.

IR $\nu_{max}^{KBr}$ cm$^{-1}$: 1754 (C=O).

NMR(CD$_3$OD)δ: 1.00–4.00 (13H, m, piperidine protons and C$\underline{H}_2$C$\underline{H}_2$CO); 3.75 (3H, s, OC$\underline{H}_3$); 6.63–7.04 (4H, m, aromatic protons).

EXAMPLE 10 p-t-Butylphenyl 1-amidino-4-piperidinepropionate hydrochloride

A mixture of 5.0 g of 1-amidino-4-piperidinepropionic acid hydrochloride and 9.2 g of bis-(p-t-butylphenyl)sulfite was stirred at room temperature for 3 hours in a solution of 40 ml of dry dimethylformamide and 20 ml of dry pyridine. The solvent was removed under reduced pressure, and ether was added to the residue to give crystals. The crystals were washed with ether and then with acetone and dissolved in methanol. After removal of any insoluble materials, ether was added to the solution to obtain 7.2 g (yield: 92%) of p-t-butylphenyl 1-amidino-4-piperidinepropionate hydrochloride as colorless crystals having a melting point of 159° to 163° C.

IR $\nu_{max}^{KBr}$ cm$^{-1}$: 1748 (C=O).

NMR(CD$_3$OD)δ: 0.84–3.84 (13H, m, piperidine protons and C$\underline{H}_2$C$\underline{H}_2$CO); 1.29 (9H, s, CH(C$\underline{H}_3$)$_3$); 6.84–7.14 (4H, m, aromatic protons).

EXAMPLE 11 p-Acetaminophenyl 1-amidino-4-piperidinepropionate hydrochloride

A mixture of 2.0 g of 1-amidino-4-piperidinepropionic acid hydrochloride and 1.29 g of p-acetaminophenol was dissolved in 20 ml of dry pyridine. To the solution was added with stirring and ice-cooling 1.75 g of dicyclohexylcarbodiimide, and the resulting mixture was stirred overnight at room temperature. The reaction mixture was filtered to give crystals which were then washed with ethyl acetate and further with ether and dried. The crystals were refluxed with 600 ml of dichloromethane, and the resulting mixture was filtered to give an insoluble substance. The substance was washed with dichloromethane and recrystallized from methanol-ethyl acetate to obtain 1.5 g (yield: 48.4%) of p-acetaminophenyl 1-amidino-4-piperidinepropionate hydrochloride as colorless crystals having a melting point of 258° to 261° C.

IR $\nu_{max}^{KBr}$ cm$^{-1}$: 1761 (C=O).

NMR(CD$_3$OD)δ: 0.89–4.05 (13H, m, piperidine protons and C$\underline{H}_2$C$\underline{H}_2$CO); 2.10 (3H, s, COC$\underline{H}_3$); 7.01–7.70 (4H, m, aromatic protons).

EXAMPLE 12 o-Allylphenyl 1-amidino-4-piperidinepropionate hydrochloride 3.7 g of bis-(o-allylphenyl)sulfite prepared from o-allylphenol and thionyl chloride was dissolved in a solution of 16 ml of dry dimethylformamide and 8 ml of dry pyridine. 2.0 g of 1-amidino-4-piperidinepropionic acid hydrochloride was added with stirring to the resulting solution, and the mixture was stirred at room temperature for 3 hours. The reaction mixture was concentrated under reduced pressure, and the residue was diluted with acetone. The mixture was poured with stirring into ether to give crystals. The crystals were washed in turn with ether, acetone and ether and dried to obtain 2.3 g (yield: 77.2%) of o-allylphenyl 1-amidino-4-piperidinepropionate hydrochloride as colorless crystals having a melting point of 116° to 119° C.

The thus obtained crystals were further purified to give crystals having a melting point of 122° to 124° C.

IR $\nu_{max}^{KBr}$ cm$^{-1}$: 1762 (C=O).

NMR(CDCl$_3$): 1.01–4.42 (13H, m, piperidine protons and C$\underline{H}_2$C$\underline{H}_2$CO); 3.36 (2H, d, C$\underline{H}_2$—Ph); 5.03–5.34 (2H, m, =C$\underline{H}_2$); 5.82–6.23 (1H, m, —C$\underline{H}$=); 6.98–7.77 (4H, m, aromatic protons).

EXAMPLE 13 p-Acetylphenyl 1-amidino-4-piperidinepropionate hydrochloride

A mixture of 2.00 g of 1-amidino-4-piperidinopropionic acid hydrochloride and 1.15 g of p-acetylphenol was suspended in 20 ml of dry pyridine. 1.74 g of dicyclohexylcarbodiimide was added with ice-cooling to the suspension, and the mixture was stirred at room temperature for 2 days. After removal of any insoluble materials, the solvent was removed under reduced pressure. Ethyl acetate was added to the residue to give crystals which were then recrystallized from ethanol-ethyl acetate to obtain 2.2 g (yield: 73.3%) of p-acetylphenyl 1-amidino-4-piperidinepropionate hydrochloride as colorless crystals having a melting point of 104° to 106° C.

IR $\nu_{max}^{KBr}$ cm$^{-1}$: 1768 (C=O);

NMR(CD$_3$OD)δ: 0.83–4.20 (13H, m, piperidine protons and C$\underline{H}_2$C$\underline{H}_2$CO); 2.69 (3H, s, COC$\underline{H}_3$); 7.30–8.49 (4H, m, aromatic protons).

EXAMPLE 14

2'-Chloro-4'-t-butylphenyl 1-amidino-4-piperidinepropionate hydrochloride 5.3 g bis-(2-chloro-4-t-butylphenyl)sulfite prepared from 2-chloro-4-t-butylphenol and thionyl chloride was dissolved in a solution of 16 ml of dry dimethylformamide end 8 ml of dry pyridine, and 2.0 g of 1-amidino-4-piperidinepropionic acid hydrochloride was added with stirring to the resulting solution, and the mixture was stirred at room temperature for 2 hours. The solvent was removed under reduced pressure. Ether was added to the residue, and the mixture was stirred to give crystals. The crystals were air-dried at room temperature and recrystallized from methanol-ethyl acetate to obtain 2.2 g (yield: 64.7%) of 2'-chloro-4'-t-butylphenyl 1-amidino-4-piperidinepropionate hydrochloride as colorless crystals having a melting point of 186° to 189° C.

IR $\nu_{max}^{KBr}$ cm$^{-1}$: 1769 (C=O).

NMR(CD$_3$OD)δ: 0.94–3.99 (13H, m, piperidine protons and C$\underline{H}_2$C$\underline{H}_2$CO); 1.34 (9H, s, C(C$\underline{H}_3$)$_3$); 7.00–7.49 (3H, m, aromatic protons).

EXAMPLE 15 p-Isopropylphenyl 1-amidino-4-piperidinepropionate hydrochloride

A mixture of 2 g of 1-amidino-4-piperidinepropionic acid hydrochloride, 4.05 g of bis-(p-isopropylphenyl)sulfite prepared from p-isopropylphenol and thionyl chloride, 10 ml of dry dimethylformamide and 5 ml of dry pyridine was stirred at room temperature for 1 hour. The solvent was removed, and ether was added to the residue to give crystals. The crystals were washed with ether and then with ethyl acetate and recrystallized from isopropyl alcohol-ethyl acetate-ether to obtain 2.9 g (yield: 97%) of p-isopropylphenyl 1-amidino-4-piperidinepropionate hydrochloride as colorless needles having a melting point of 119° to 121° C.

IR $\nu_{max}^{KBr}$ cm$^{-1}$: 1755 (C=O).

NMR(CD$_3$OD)δ: 1.24 (6H, d, J=7.2 Hz, C$\underline{H}_3$×2); 1.0–2.0 (7H, m, β-H$_2$, 3- and 5-H$_2$, 4-H); 2.7–4.0 (5H, m, 2- and 6-H$_2$, C$\underline{H}$<); 6.99, 7.26 (each 2H, each d, J=8.4 Hz, aromatic protons).

EXAMPLE 16

2'-Naphthyl 1-amidino-4-piperidinepropionate hydrochloride

A mixture of 2 g of 1-amidino-4-piperidinepropionic acid hydrochloride, 4.3 g of bis-(2-naphthyl)sulfite prepared from β-naphthol and thionyl chloride, 10 ml of dry dimethylformamide and 5 ml of dry pyridine was stirred at room temperature for 3 hours. The solvent was removed, and ether was added to the residue to give crystals. The crystals were recrystallized from methanol-ether to obtain 2.4 g (yield: 78%) of 2'-naphthyl 1-amidino-4-piperidinepropionate hydrochloride as colorless needles having a melting point of 185° to 187° C.

IR $\nu_{max}^{KBr}$ cm$^{-1}$: 1745 (C=O).

NMR(CD$_3$OD)δ: 1.0–2.0 (7H, m, β-H$_2$, 3- and 5-H$_2$, 4-H); 2.68 (2H, t, J=7,8 Hz, α-H$_2$); 2.9–4.0 (4H, m, 2- and 6-H$_2$); 7.1–8.0 (7H, m, aromatic protons).

EXAMPLE 17

1'-Naphthyl 1-amidino-4-piperidinepropionate hydrochloride

A mixture of 2 g of 1-midino-4-piperidinepropionic acid hydrochloride, 4.25 g of bis-(1-naphthyl)sulfite prepared from α-naphthol and thionyl chloride, 10 ml of dry dimethylformamide and 4 ml of dry pyridine was stirred at room temperature for 1 hour. The solvent was removed, and the residue was treated with ethyl acetate to give crystals. The crystals were washed with ethyl acetate to obtain 2.9 g (yield: 94%) of 1'-naphthyl 1-amidino-4-piperidinepropionate hydrochloride as light brown needles having a melting point of 187° to 190° C.

IR $\nu_{max}^{KBr}$ cm$^{-1}$: 1755 (C=O).

NMR(CD$_3$OD)δ: 1.0–2.0 (7H, m, β-H$_2$, 3- and 5-H$_2$, 4-H); 2.78 (2H, t, J=7.2 Hz, α-H$_2$); 3.0–4.0 (4H, m, 2- and 6-H$_2$); 7.1–8.0 (7H, m, aromatic protons).

EXAMPLE 18

2',4'-Dimethylphenyl 1-amidino-4-piperidinepropionate hydrochloride

A mixture of 4.0 g of 1-amidino-4-piperidinepropionic acid hydrochloride and 6.9 g of bis-(2,4-dimethylphenyl)sulfite prepared from 2,4-dimethylphenol and thionyl chloride was added to a solution of 34 ml of dry dimethylformamide and 17 ml of dry pyridine, and the resulting mixture was allowed to stand at room temperature for 6 hours. The solvent was removed under reduced pressure, and ethyl acetate was added to the residue to give crystals. The crystals were recrystallized from methanol-ether to obtain 4.5 g (yield: 78%) of 2',4'-dimethylphenyl 1-amidino-4-piperidinepropionate hydrochloride as colorless needles having a melting point of 191° to 193° C.

IR $\nu_{max}^{KBr}$ cm$^{-1}$: 1745 (C=O).

NMR(CD$_3$OD)δ: 0.96–3.96 (13H, m, piperidine protons and C$\underline{H}_2$C$\underline{H}_2$CO); 2.08 (3H, s, 4'—CH$_3$); 2.26 (3H, s, 2'—CH$_3$); 6.66–7.04 (3H, m, aromatic protons).

EXAMPLE 19 p-Fluorophenyl 1-amidino-4-piperidinepropionate hydrochloride

A mixture of 2.00 g of 1-amidino-4-piperidinepropionic acid hydrochloride and 0.95 g of p-fluorophenol was suspended in 20 ml of dry pyridine. To the suspension was added with stirring and ice-cooling 1.74 g of dicyclohexylcarbodiimide and the resulting mixture was allowed to stand at room temperature for 4 days. After removal of any insoluble materials, the filtrate was concentrated under reduced pressure. Ethyl acetate was added to the residue to give crystals which were then recrystallized from methanol-ether to obtain 1.4 g (yield: 50.0%) of p-fluorophenyl 1-amidino-4-piperidinepropionate hydrochloride as colorless crystals having a melting point of 131° to 133° C.

IR $\nu_{max}^{KBr}$ cm$^{-1}$: 1750 (C=O).

NMR(CD$_3$OD)δ: 0.88–3.96 (13H, m, piperidine protons and C$\underline{H}_2$C$\underline{H}_2$CO); 6.80–7.15 (4H, m, aromatic protons).

EXAMPLE 20 p-Cyclohexylphenyl 1-amidino-4-piperidinepropionate hydrochloride

A mixture of 8 g of bis-(p-cyclohexylphenyl)sulfite prepared from p-cyclohexylphenol and thionyl chloride and 4 g of 1-amidino-4-piperidinepropionic acid hydrochloride was dissolved in a solution of 20 ml of dry dimethylformamide and 8 ml of dry pyridine, and the resulting solution was stirred at room temperature for 2.5 hours. The solvent was removed, and the residue was treated with ethyl acetate to give crystals. The crystals were recrystallized from isopropanol-ether to obtain 5.6 g (yield: 83.6%) of p-cyclohexylphenyl 1-amidino-4-piperidine propionate hydrochloride as colorless crystals having a melting point of 115° to 116° C.

IR $\nu_{max}^{KBr}$ cm$^{-1}$: 1760 (C=O).

NMR(CD$_3$OD)δ: 1.00–4.00 (24H, m, piperidine protons, cyclohexane protons and C$\underline{H}_2$C$\underline{H}_2$CO); 6.8–7.20 (4H, m, aromatic protons).

EXAMPLE 21 p-(α,α-Dimethylbenzyl)phenyl 1-amidino-4-piperidinepropionate hydrochloride

A mixture of 9.6 g of bis-[p-(α,α-dimethylbenzyl)phenyl]sulfite prepared from p-(α,α-dimethylbenzyl)phenol and thionyl chloride and 4 g of 1-amidino-4-piperidinepropionic acid hydrochloride was added to a solution of 20 ml of dry dimethylformamide and 8 ml of dry pyridine, and the resulting solution was stirred at room temperature for 2.5 hours. After removal of the solvent, ethyl acetate was added to the residue, and the mixture was stirred to give crystals. The crystals were washed with ethyl acetate and then with ether and recrystallized from isopropanol-ether to obtain 5.5 g (yield: 75.3%) of p-(α,α-dimethylbenzyl)phenyl 1-amidino-4-piperidinepropionate hydrochloride as colorless crystals having a melting point of 155° to 156° C.

The thus obtained crystals were recrystallized twice to give crystals having a melting point of 195° to 196° C.

IR $\nu_{max}^{KBr}$ cm$^{-1}$: 1765 (C=O).

NMR(CD$_3$OD)δ: 1.0–4.0 (13H, m, piperidine protons and C$\underline{H}_2$C$\underline{H}_2$CO); 1.64 (6H, s, >C(C$\underline{H}_3$)$_2$); 6.80–7.30 (4H, m, aromatic protons).

EXAMPLE 22

4'-Formyl-2'-methoxyphenyl 1-amidino-4-piperidinepropionate hydrochloride

A mixture of 4.7 g of 1-amidino-4-piperidinepropionic acid hydrochloride, 3 g of vaniline, 4.1 g of dicyclohexylcarbodiimide, 20 ml of dry dimethylformamide and 10 ml of dry pyridine was stirred at room temperature for 24 hours. After removal of any insoluble materials, the solvent was removed. The residue was treated with ethyl acetate to give white powder. The powder was washed with ethyl acetate and then with ether and recrystallized from isopropanol-ether to obtain 5.8 g (yield: 79.5%) of 4'-formyl-2'-methoxyphenyl 1-amidino-4-piperidinepropionate hydrochloride as colorless crystals having a melting point of 98° to 105° C.

IR $\nu_{max}^{KBr}$ cm$^{-1}$: 1700, 1750, 1770 (C=O).

NMR(CD$_3$OD)δ: 1.04–4.20 (13H, m, piperidine protons and C$\underline{H}_2$C$\underline{H}_2$CO); 3.95 (3H, s, OC$\underline{H}_3$); 7.50–8.0 (3H, m, aromatic protons); 10.4 (1H, s, CHO).

EXAMPLE 23 p-Aminosulfonylphenyl 1-amidino-4-piperidinepropionate hydrochloride

A mixture of 4.7 g of 1-amidino-4-piperidinepropionic acid hydrochloride, 3.5 g of p-hydroxybenzene sulfonamide, 4.1 g of dicyclohexylcarbodiimide, 10 ml of dry dimethylformamide and 20 ml of dry pyridine was stirred at room temperature for 24 hours. After removal of any insoluble materials, the solvent was removed. The residue was treated with ethyl acetate and then with ether to give crystals. The crystals were dissolved in methanol, and any insoluble materials were removed by filtration. Ether was added to the filtrate to obtain 4.5 g (yield: 57.7%) of p-aminosulfonylphenyl 1-amidino-4-piperidinepropionate hydrochloride as yellow crystals having a melting point of 206° to 209° C.

IR $\nu_{max}^{KBr}$ cm$^{-1}$: 1760 (C=O).

NMR(CD$_3$OD)δ: 1.04–4.20 (13H, m, piperidine protons and C$\underline{H}_2$C$\underline{H}_2$CO); 7.44–8.28 (4H, m, aromatic protons).

EXAMPLE 24 m-Trifluoromethylphenyl 1-amidino-4-piperidinepropionate hydrochloride

A mixture of 4.0 g of 1-amidino-4-piperidinepropionic acid hydrochloride and 2.75 g of m-trifluoromethylphenol was suspended in 27 ml of dry pyridine. To the suspension was added 3.5 g of dicyclohexylcarbodiimide, and the resulting mixture was stirred at room temperature for 6 hours. After removal of any insoluble materials, the solvent was removed. The residue was washed with ether, dissolved in chloroform and then stirred. After removal of any insoluble materials, the filtrate was washed twice with a saturated sodium chloride solution and then dried over anhydrous sodium sulfate. The solvent was removed under reduced pressure to obtain 4.0 g (yield: 62.0%) of m-trifluoromethylphenyl 1-amidino-4-piperidinepropionate hydrochloride as colorless crystals having a melting point of 97° to 100° C.

IR $\nu_{max}^{KBr}$ cm$^{-1}$: 1760 (C=O).

NMR(CDCl$_3$)δ: 0.92–4.52 (13H, m, piperidine protons and C$\underline{H}_2$C$\underline{H}_2$CO); 7.20–7.92 (4H, m, aromatic protons).

EXAMPLE 25 p-Formylphenyl 1-amidino-4-piperidinepropionate hydrochloride

A mixture of 4.0 g of 1-amidino-4-piperidinepropionic acid hydrochloride and 2.1 g of p-hydroxybenzaldehyde was suspended in 20 ml of dry pyridine. 3.5 g of dicyclohexylcarbodiimide was added with stirring to the suspension, and the resulting mixture was stirred overnight at room temperature. After removal of any insoluble materials, the filtrate was concentrated under reduced pressure. Ethyl acetate was added to the residue, and the mixture was stirred to give crystals. The crystals were recrystallized from methanol-ether to obtain 2.1 g (yield: 36.4%) of p-formylphenyl 1-amidino-4-piperidinepropionate hydrochloride as colorless crystals having a melting point of 144° to 147° C.

IR $\nu_{max}^{KBr}$ cm$^{-1}$: 1700, 1760 (C=O).

NMR(CD$_3$OD)δ: 0.92–4.16 (13H, m, piperidine protons and C$\underline{H}_2$C$\underline{H}_2$CO); 7.40–8.20 (4H, m, aromatic protons); 10.16 (1H, s, C$\underline{H}$O).

EXAMPLE 26 p-Cyanophenyl 1-amidino-4-piperidinepropionate hydrochloride

A mixture of 4.0 g of 1-amidino-4-piperidinepropionic acid hydrochloride, 2.0 g of p-cyanophenol and 3.5 g of dicyclohexylcarbodiimide was stirred overnight at room temperature in 20 ml of dry pyridine. Any insoluble materials were filtered, washed with pyridine and extracted with a solution of 20 ml of water and 20 ml of t-butanol, followed by stirring for about 20 minutes. The filtrate, washings and extract were combined together, and the solvent was removed under reduced pressure. The residue was recrystallized from water to obtain 3.4 g (yield: 59%) of p-cyanophenyl 1-amidino-4-piperidinepropionate hydrochloride as colorless crystals having a melting point of 164.5° to 169° C.

IR $\nu_{max}^{KBr}$ cm$^{-1}$: 2240 (CN), 1765 (C=O);

NMR(CD$_3$OD)δ: 1.00–4.10 (13H, m, piperidine protons and C$\underline{H}_2$C$\underline{H}_2$CO); 7.40–8.10 (4H, m, aromatic protons).

EXAMPLE 27 o-Cyanophenyl 1-amidino-4-piperidinepropionate hydrochloride

A mixture of 4.0 g of 1-amidino-4-piperidinepropionic acid hydrochloride, 2.0 g of o-cyanophenol and 3.5 g of dicyclohexylcarbodiimide was stirred at room temperature for 24 hours in 20 ml of dry pyridine. Any insoluble materials were filtered and washed with dry pyridine. The filtrate and washings were combined together, and the solvent was removed under reduced pressure. Ethyl acetate was added to the residue to give crystals which were then recrystallized from water to obtain 2.1 g (yield: 37%) of o-cyanophenyl 1-amidino-4-piperidinepropionate as colorless crystals having a melting point of 159.5° to 162.5° C.

IR $\nu_{max}^{KBr}$ cm$^{-1}$: 2240 (CN), 1775 (C=O);

NMR (CD$_3$OD)δ: 1.00–4.10 (13H, m, piperidine protons and C$\underline{H}_2$C$\underline{H}_2$CO); 7.40–8.00 (4H, m, aromatic protons).

EXAMPLE 28 o-Methylphenyl 1-amidino-4-piperidinepropionate hydrochloride

A mixture of 6.7 g of bis-(o-methylphenyl)sulfite prepared from o-methylphenol and thionyl chloride, 4 g of 1-amidino-4-piperidinepropionic acid hydrochloride was stirred at room temperature for 24 hours in a solution of 20 ml of dry dimethylformamide and 6 ml of dry pyridine. The solvent was removed under reduced pressure, and 50 ml of ethyl acetate and 20 ml of ether were added to the residue to give crystals. The crystals were recrystallized in turn from isopropanol-ether, methanol-ether and water to obtain 2.1 g (yield: 38%) of o-methylphenyl 1-amidino-4-piperidinepropionate hydrochloride as colorless crystals having a melting point of 184° to 185.5° C.

IR $\nu_{max}^{KBr}$ cm$^{-1}$: 1750 (C=O).

NMR(CD$_3$OD)δ: 1.00–4.05 (13H, m, piperidine protons and C$\underline{H}_2$C$\underline{H}_2$CO); 2.14 (3H, s, C$\underline{H}_3$); 6.90–7.30 (4H, m, aromatic protons).

EXAMPLE 29 o-Methylphenyl 1-amidino-4-piperidinepropionate hydrochloride

A mixture of 4 g of 1-amidino-4-piperidinepropionic acid hydrochloride, 1.9 of o-methylphenol, 3.5 g of dicyclohexylcarbodiimide and 20 ml of dry pyridine was stirred overnight at room temperature. Any insoluble materials were filtered and washed with pyridine. The filtrate and washings were combined together, and the solvent was removed under reduced pressure. Ethyl acetate and ether were added to the residue to give crystals. After being air-dried, the crystals were recrystallized from water to obtain 3 g (yield: 54%) of -methylphenyl 1-amidino-4-piperidinepropionate hydrochloride as colorless prisms having a melting point of 184° to 185.5° C. The IR and NMR spectra of the compound were identical with those of the compound obtained in Example 28.

EXAMPLE 30

3'-Pyridyl 1-amidino-4-piperidinepropionate hydrochloride

A mixture of 4.71 g of 1-amidino-4-piperidinepropionic acid hydrochloride, 1.95 g of 3-hydroxypyridine, 4.13 g of dicyclohexylcarbodiimide, 40 ml of dry dimethylformamide and 20 ml of dry pyridine was stirred at room temperature for 19 hours. After removal of any insoluble materials, the solvent was removed. The residue was washed with ethyl acetate and dissolved in methanol. Any insoluble materials were removed by filtration, and ethyl acetate was added to the filtrate to give crystals. The crystals were washed with ethyl acetate and then with ether to obtainn 6.2 g (yield: 99%) of 3'-pyridyl 1-amidino-4-piperidinepropionate hydrochloride as colorless needles having a melting point of 177° to 179° C.

IR $\nu_{max}^{KBr}$ cm$^{-1}$: 1765 (C=O).

NMR(CD$_3$OD)δ: 1.0–2.1 (7H, m, 3- and 5-H$_2$, 4-H and β-H$_2$); 2.84 (2H, t, J=7.6 Hz, α-H$_2$); 3.0–4.2 (4H, m, 2- and 6-H$_2$); 7.7–8.9 (4H, m, pyridine protons).

EXAMPLE 31 o-Phenylphenyl 1-amidino-4-piperidinepropionate hydrochloride

A mixture of 4 g of 1-amidino-4-piperidinepropionic acid hydrochloride, 9.3 g of bis-(o-phenylphenyl)sulfite prepared from o-phenylphenol and thionyl chloride, 40 ml of dry dimethylformamide and 20 ml of dry pyridine was stirred at room temperature for 4 hours. The solvent was removed undeer reduced pressure, and the residue was recrystallized from water and washed with ethyl acetate and then with ether to obtain 3.45 g (yield: 52%) of o-phenylphenyl 1-amidino-4-piperidinepropionate hydrochloride as colorless needles having a melting point of 160° to 162° C.

IR $\nu_{max}^{KBr}$ cm$^{-1}$: 1755 (C=O).

NMR(CD$_3$OD)δ: 0.8–1.9 (7H, m, 3- and 5-H$_2$, 4-H and β-H$_2$); 2.52 (2H, t, J=7.0 Hz, α-H$_2$); 2.8–4.1 (4H, m, 2- and 6-H$_2$); 7.3–7.9 (9H, m, aromatic protons).

EXAMPLE 32 p-Phenylphenyl 1-amidino-4-piperidinepropionate hydrochloride

A mixture of 4 g of 1-amidino-4-piperidinepropionic acid hydrochloride, 9.3 g of bis-(p-phenylphenyl)sulfite prepared from p-phenylphenol and thionyl chloride, 40 ml of dry dimethylformamide and 8 ml of dry pyridine was stirred at room temperature for 3 hours. The solvent was removed under reduced pressure, and the residue was crystallized from methanol-ethyl acetate to obtain 4 g (yield: 61%) of p-phenylphenyl 1-amidino-4-piperidinepropionate hydrochloride as colorless needls having a melting point of 200° to 203° C.

IR $\nu_{max}^{KBr}$ cm$^{-1}$: 1755 (C=O).

NMR(CD$_3$OD)$\delta$: 1.0–2.0 (7H, m, 3- and 5-H$_2$, 4-H and $\beta$-H$_2$); 2.61 (2H, t, J=6.8 Hz, $\alpha$-H$_2$); 2.8–4.0 (4H, m, 2- and 6-H$_2$); 7.0–7.6 (9H, m, aromatic protons).

EXAMPLE 33

2', 4', 6'-Trimethylphenyl 1-amidino-4-piperidinepropionate hydrochloride

A mixture of 4 g of 1-amidino-4-piperidinepropionic acid hydrochloride, 2.3 g of 2,4,6-trimethylphenol and 3.5 g of dicyclohexylcarbodiimide was stirred overnight at room temperature in dry pyridine. Any insoluble materials were filtered and washed with dry pyridine and then with a solution of 25 ml of t-butanol and 25 ml of water. The filtrate and washings were combined together and concentrated under reduced pressure. 50 ml of ethyl acetate was added to the residue, and the mixture was stirred to give crystals. The crystals were recrystallized from water to obtain 3.3 g (yield: 55%) of 2',4',6'-trimethylphenyl 1-amidino-4-piperidinepropionate hydrochloride as colorless crystals having a melting point of 220° to 223° C.

IR $\nu_{max}^{KBr}$ cm$^{-1}$: 1750 (C=O).

NMR(CD$_3$OD)$\delta$: 1.00–4.16 (13H, m, piperidine protons and C$\underline{H}_2$C$\underline{H}_2$CO); 2.12 (6H, s, 2,6—C$\underline{H}_3$); 2.26 (3H, s, 4-C$\underline{H}_3$); 6.92 (2H, s, aromatic protons).

EXAMPLE 34

2',6'-Dimethylphenyl 1-amidino-4-piperidinepropionate hydrochloride 7.4 g of bis-(2,6-dimethylphenyl)sulfite prepared from 2.6-dimethylphenol and thionyl chloride was dissolved in a solution of 36 ml of dry dimethylformamide and 18 ml of dry pyridine. To the solution was added with stirring 4.0 g of 1-amidino-4-piperidinepropionic acid hydrochloride, and the resulting mixture was allowed to stand at room temperature for 4 days. The solvent was removed under reduced pressure, and ether was added to the residue to give crystals. The crystals were wased with ether and then with ethyl acetate and recrystallized from water to obtain 3.3 g (yield: 57%) of 2',6'-dimethylphenyl 1-amidino-4-piperidinepropionate hydrochloride as pale yellow crystals having a melting point of 191° to 194° C.

IR $\nu_{max}^{KBr}$ cm$^{-1}$: 1740 (C=O).

NMR(CD$_3$OD)$\delta$: 0.96–4.32 (13H, m, piperidine protons and C$\underline{H}_2$C$\underline{H}_2$CO); 2.24 (6H, s, 2,6-C$\underline{H}_3$); 7.24–7.60 (3H, m, aromatic protons).

EXAMPLE 35

5'-Indanyl 1-amidino-4-piperidinepropionate hydrochloride 7.0 g of bis-(5-indanyl)sulfite prepared from 5-indanol and thionyl chloride was dissolved in a solution of 25 ml of dry dimethylformamide and 12 ml of dry pyridine. To the solution was added with stirring 3.0 g of 1-amidino-4-piperidinepropionic acid hydrochloride, and the resulting mixture was allowed to stand for 4 hours. The solvent was removed under reduced pressure, and ethyl acetate was added to the residue to give crystals. The crystals were washed with ethyl acetate and then with ether and recrystallized from methanol-ether to obtain 3.6 g (yield: 80%) of 5'-indanyl 1-amidino-4-piperidinepropionate hydrochloride as colorless crystals having a melting point of 184° to 188° C.

IR $\nu_{max}^{KBr}$ cm$^{-1}$: 1760 (C=O).

NMR(CD$_3$OD)$\delta$: 0.84–4.32 (19H, m, piperidine protons, C$\underline{H}_2$C$\underline{H}_2$CO and C$\underline{H}_2$C$\underline{H}_2$CH); 7.00–7.64 (3H, m, aromatic protons).

EXAMPLE 36 p-Methoxycarbonylphenyl 1-amidino-4-piperidinepropionate hydrochloride

A mixture of 5 g of 1-amidino-4-piperidinepropionic acid hydrochloride, 3.23 g of methyl p-hydroxybenzoate, 4.38 g of dicyclohexylcarbodiimide, 100 ml of dry dimethylformamide and 20 ml of dry pyridine was stirred at room temperature for 24 hours, and the mixture was treated in the same procedure as in Example 11. The crystals obtained were recrystallized from isopropanolether to obtain 5.7 g (yield: 72.7%) of p-methoxycarbonylphenyl 1-amidino-4-piperidinepropionate hydrochloride as colorless needles having a melting point of 163° to 164.5° C.

IR $\nu_{max}^{KBr}$ cm$^{-1}$: 1700, 1730, 1755 (C=O).

EXAMPLE 37 o-Acetaminophenyl 1-amidino-4-piperidinepropionate hydrochloride

A mixture of 4.0 g of 1-amidino-4-piperidinepropionic acid hydrochloride, 2.6 g of o-acetaminophenol was dissolved in 40 ml of dry pyridine. To the solution was added with ice-cooling and stirring 3.5 g of dicyclohexylcarbodiimide, and the resulting mixture was allowed to stand at room temperature for 44 hours. After removal of any insoluble materials, the solvent was removed under reduced pressure. The residue was washed with ethyl acetate, and dry ether was then added to the residue to give crystals. The crystals were washed with ether several times, then with warm dichloromethane and finally with ethyl acetate. Dry ether was added to the crystals, and the mixture was evaporated to dryness to obtain 5.8 g (yield: 92.7%) of o-acetaminophenyl 1-amidino-4-piperidinepropionate hydrochloride as hygroscopic crystals.

IR $\nu_{max}^{KBr}$ cm$^{-1}$: 1750 (C=O).

NMR(CD$_3$OD)$\delta$: 0.92–4.26 (13H, m, piperidine protons and CH$_2$CH$_2$CO); 2.40 (3H, s, COCH$_3$); 7.28–8.20 (4H, m, aromatic protons).

EXAMPLE 38

5',6',7',8'-Tetrahydro-2'-naphthyl 1-amidino-4-piperidinepropionate hydrochloride A mixture of 4 g of 1-amidino-4-piperidinepropionic acid hydrochloride, 2.5 g of 5,6,7,8-tetrahydro-2-naphthol, 4 g of dicyclohexylcarbodiimide and 25 ml of dry pyridine was stirred on an oil bath at room temperature for 1 day and then at 50° C. for 6 hours. After removal of any insoluble materials, the solvent was removed under reduced pressure. The residue was washed with ethyl acetate and then with ether and dissolved in a small amount of isopropanol. Water was added to the solution to give crystals which were then washed with ethyl acetate and further with ether to obtain 3.5 g (yield: 56.5%) of 5',6',7',8'-tetrahydro-2'-naphthyl 1-amidino-4-piperidinepropionate hydrochloride as colorless crystals having a melting point of 113° to 115° C.

IR $\nu_{max}^{KBr}$ cm$^{-1}$: 1758 (C=O).

NMR(CD$_3$OD)$\delta$: 1.70–1.94 (8H, m, —(C$\underline{H}_2$)$_4$—); 1.04–4.20 (13H, m, piperidine protons and C$\underline{H}_2$C$\underline{H}_2$CO); 7.00–7.44 (3H, m, aromatic protons).

EXAMPLE 39 p-Nitrophenyl 1-amidino-4-piperidinepropionate hydrochloride

A mixture of 5.0 g of 1-amidino-4-piperidinepropionic acid hydrochloride, 7.6 g of bis-(p-nitrophenyl)-sulfite prepared from p-nitrophenol and thionyl chloride, 20 ml of dry dimethylformamide and 6 ml of dry pyridine was stirred at room temperature for 22 hours. The solvent was removed under reduced pressure, and 70 ml of ethyl acetate and 30 ml of ether were added to the residue. The mixture was well stirred, and the supernatant solution was removed by decantation. 50 ml of ether was added to the residue. Followed by sufficient stirring of the mixture, the supernatant solution was removed by decantation. A small amount of water was added to the residue, and the mixture was stimulated to give crystals. Acetone was added to the crystals, and the mixture was stirred, thereby separating the crystals by filtration. The crystals were washed with acetone and then with ether and dried to obtain 3.2 g of p-nitrophenyl 1-amidino-4-piperidinepropionate hydrochloride as colorless crystals having a melting point of 131° to 136° C.

IR $\nu_{max}^{KBr}$ cm$^{-1}$: 1770 (C=O).

NMR(DMSO-d$_6$)$\delta$: 0.92–4.08 (13H, m, piperidine protons and C$\underline{H}_2$C$\underline{H}_2$CO); 6.90–7.10 (6H, m, N$\underline{H}_2$ and aromatic protons); 7.80–8.00 (2H, m, aromatic protons).

EXAMPLE 40

Phenylthio 1-amidino-4-piperidinepropionate hydrochloride

A mixture of 2.4 g of 1-amidino-4-piperidinepropionic acid hydrochloride, 1.1 g of thiophenol, 2.1 g of dicyclohexylcarbodiimide and 15 ml of dry dimethylformamide was stirred at room temperature for 17 hours. After removal of any insoluble materials, the solvent was removed. The residue was washed with ether and then with t-butanol to obtain 1.2 g (yield: 36.4%) of phenylthio 1-amidino-4-piperidinepropionate hydrochloride as colorless crystals having a melting point of 168° to 170° C.

IR $\nu_{max}^{KBr}$ cm$^{-1}$: 1710 (C=O).

NMR(CD$_3$OD)$\delta$: 1.0–4.16 (13H, m, piperidine protons and C$\underline{H}_2$C$\underline{H}_2$CO); 7.56 (5H, s, aromatic protons).

EXAMPLE 41 p-t-Butylphenylthio 1-amidino-4-piperidinepropionate hydrochloride

A mixture of 3 g of 1-amidino-4-piperidinepropionic acid hydrochloride, 2.2 g of p-t-butyl thiophenol, 2.6 g of dicyclohexylcarbodiimide and 18 ml of dry dimethylformamide was stirred at room temperature for 10 hours. After removal of any insoluble materials, the solvent was removed under reduced pressure. The residue was washed with ether and dissolved in t-butanol. Ether was added to the solution to give an oily substance. Water was added to the oily substance, and the mixture was allowed to stand overnight in cold conditions to give crystals. The crystals were washed with ethyl acetate and then with ether and air-dried to obtain 2.3 g (yield: 46.9%) of p-t-butylphenylthio 1-amidino-4-piperidinepropionate hydrochloride as colorless crystals having a melting point of 86° to 88° C.

IR $\nu_{max}^{KBr}$ cm$^{-1}$: 1710 (C=O).

NMR(CD$_3$OD)$\delta$: 1.00–4.10 (13H, m, piperidine protons and C$\underline{H}_2$C$\underline{H}_2$CO); 1.40 (9H, s, C(C$\underline{H}_3$)$_3$); 7.50–7.84 (4H, m, aromatic protons).

EXAMPLE 42

Phenyl 1-amidino-4-piperidinecarboxylate hydrochloride

A mixture of 826 mg of 1-amidino-4-piperidinecarboxylic acid hydrochloride and 1.4 g of diphenyl sulfite was stirred overnight at room temperature in a solution of 10 ml of dry dimethylformamide and 4 ml of dry pyridine. The solvent was removed under reduced pressure, and the residue was washed three times with 20 ml of ether. 10 ml of acetone was added to the residue, and the mixture was stirred to give crystals. The crystals were washed with acetone and dried to obtain 600 mg (yield: 53%) of phenyl 1-amidino-4-piperidinecarboxylate hydrochloride as crystalline powder having a melting point of 155.5° to 161.5° C.

IR $\nu_{max}^{KBr}$ cm$^{-1}$: 1750 (C=O).

NMR(CD$_3$OD)$\delta$: 1.50–4.00 (9H, m, piperidine protons); 6.90–7.40 (5H, m, aromatic protons).

EXAMPLE 43 o-Benzyloxycarbonylphenyl 1-amidino-4-piperidinecarboxylate hydrochloride

A mixture of 826 mg of 1-amidino-4-piperidinecarboxylic acid hydrochloride and 3.0 g of bis-(o-benzyloxycarbonylphenyl)sulfite was stirred overnight at room temperature in a solution of 10 ml of dry dimethylformamide and 4 ml of dry pyridine. The solvent was removed under reduced pressure, and the residue was washed three times with ether. 10 ml of acetone and 30 ml of ethyl acetate were added to the residue, and the mixture was stimulated to give crystals. The crystals were washed with hot ethyl acetate to obtain 1,015 mg (yield: 61%) of o-benzyloxycarbonylphenyl 1-amidino-4-piperidinecarboxylate hydrochloride as colorless crystals having a melting point of 140.5° to 147° C.

IR $\nu_{max}^{KBr}$ cm$^{-1}$: 1740, 1710 (C=O).

NMR(CD$_3$OD)$\delta$: 1.50–4.00 (9H, m, piperidine protons); 5.20 (2H, s, C$\underline{H}_2$—Ph); 6.96–8.00 (9H, m, aromatic protons).

EXAMPLE 44

2',4'-Dichlorophenyl 1-amidino-4-piperidinecarboxylate hydrochloride

A mixture of 2.0 g of 1-amidino-4-piperidinecarboxylic acid hydrochloride and 7.2 g of bis-(2,4-dichlorophenyl)sulfite was stirred at room temperature for 4 hours in a solution of 18 ml of dry dimethylformamide and 9 ml of dry pyridine. The solvent was removed under reduced pressure, and the residue was washed three times with ether. Acetone was added to the residue, and the mixture was stirred to give crystals. The crystals were washed with ethyl acetate and then with ether and recrystallized from methanol-ether to obtain 1.27 g (yield: 37.4%) of 2',4'-dichlorophenyl 1-amidino-4-piperidinecarboxylate hydrochloride as colorless crystals having a melting point of 215° to 218.5° C.

IR $\nu_{max}^{KBr}$ cm$^{-1}$: 1762 (C=O).

NMR(CD$_3$OD)δ: 1.67–4.28 (9H, m, piperidine protons); 7.31–7.82 (3H, m, aromatic protons).

EXAMPLE 45 p-Chlorophenyl 1-amidino-4-piperidinecarboxylate hydrochloride

A mixture of 1.5 g of 1-amidino-4-piperidinecarboxylic acid hydrochloride and 8.8 g of bis-(p-chlorophenyl)sulfite was stirred at room temperature for 1 hour in a solution of 14 ml of dry dimethylformamide and 7 ml of dry pyridine. The solvent was removed under reduced pressure, and the residue was washed twice with dry ether. Acetone was added to the residue to give crystals. The crystals were washed with ether and then with ethyl acetate and recrystallized from methanol-ether to obtain 1.62 g (yield: 70.4%) of p-chlorophenyl 1-amidino-4-piperidinecarboxylate hydrochloride as colorless crystals having a melting point of 196° to 198° C.

IR $\nu_{max}^{KBr}$ cm$^{-1}$: 1744 (C=O).

NMR(CD$_3$OD)δ: 1.65–4.15 (9H, m, piperidine protons); 7.19–7.72 (4H, m, aromatic protons).

EXAMPLE 46 p-Methylphenyl 1-amidino-4-piperidinecarboxylate hydrochloride

A mixture of 1.5 g of 1-amidino-4-piperidinecarboxylic acid hydrochloride and 7.6 g of bis-(p-methylphenyl)sulfite was stirred at room temperature for 1.5 hours in a solution of 7 ml of dry dimethylformamide and 7 ml of dry pyridine. The solvent was removed under reduced pressure, and ether was added to the residue to give crystals. After being washed with ether and then with ethyl acetate, the crystals were reprecipitated from methanol-ether and recrystallized from isopropanol-isopropyl ether to obtain 2.15 g (yield: 99.6%) of p-methylphenyl 1-amidino-4-piperidinecarboxylate hydrochloride as colorless crystals having a melting point of 187° to 189° C.

IR $\nu_{max}^{KBr}$ cm$^{-1}$: 1742 (C=O).

NMR(CD$_3$OD)δ: 1.50–4.00 (9H, m, piperidine protons); 2.30 (3H, s, CH$_3$); 6.61–7.23 (4H, m, aromatic protons).

EXAMPLE 47 p-Methoxyphenyl 1-amidino-4-piperidinecarboxylate hydrochloride

A mixture of 1.5 g of 1-amidino-4-piperidinecarboxylic acid hydrochloride and 7.7 g of bis-(p-methoxyphenyl)sulfite was stirred at room temperature for 18 hours in a solution of 16 ml of dry dimethylformamide and 8 ml of dry pyridine. The solvent was removed under reduced pressure, and ether was added to the residue to give crystals. The crystals were washed with ether twice and then with ethyl acetate and recrystallized from methanol-ether to obtain 1.9 g (yield: 83.7%) of p-methoxyphenyl 1-amidino-4-piperidinecarboxylate hydrochloride as colorless crystals having a melting point of 198° to 203° C.

IR $\nu_{max}^{KBr}$ cm$^{-1}$: 1739 (C=O).

NMR(CD$_3$OD)δ: 1.48–4.01 (9H, m, piperidine protons); 3.75 (3H, s, OCH$_3$); 6.73–7.05 (4H, m, aromatic protons).

EXAMPLE 48 p-t-Butylphenyl 1-amidino-4-piperidinecarboxylate hydrochloride

A mixture of 1.0 g of 1-amidino-4-piperidinecarboxylic acid hydrochloride and 3.3 g of bis-(p-t-butylphenyl)sulfite was stirred at room temperature for 2.5 hours in a solution of 10 ml of dry dimethylformamide and 5 ml of dry pyridine. The solvent was removed under reduced pressure, and dry ether was added to the residue to give crystals. The crystals were washed with dry ether and then with ethyl acetate and recrystallized from methanol-ether to obtain 1.0 g (yield: 61.4%) of p-t-butylphenyl 1-amidino-4-piperidinecarboxylate hydrochloride as colorless crystals having a melting point of 211° to 213° C.

The thus obtained crystals were recrystallized twice to give crystals having a melting point of 222° to 223° C.

IR $\nu_{max}^{KBr}$ cm$^{-1}$: 1742 (C=O).

NMR(CD$_3$OD)δ: 1.38 (9H, s, C(CH$_3$)$_3$); 1.65–4.15 (9H, m, piperidine protons); 7.04–7.74 (4H, m, aromatic protons).

EXAMPLE 49 p-(α,α-Dimethylbenzyl)phenyl 1-amidino-4-piperidinecarboxylate hydrochloride:

A mixture of 10.9 g of bis[p-(α,α-dimethylbenzyl)phenyl]sulfite prepared from p-[α,α-dimethylbenzyl)phenol and thionyl chloride, 4 g of 1-amidino-4-piperidinecarboxylic acid hydrochloride, 20 ml of dry dimethylformamide and 8 ml of dry pyridine was stirred at room temperature for 18 hours. The solvent was removed under reduced pressure to give an oily substance which was then treated with ethyl acetate to give powder. The powder was recrystallized from isopropanol-ether to obtain 5.3 g (yield: 68.8%) of p-(α,α-dimethylbenzyl)phenyl 1-amidino-4-piperidinecarboxylate hydrochloride as colorless crystals having a melting point of 166° to 168° C.

IR $\nu_{max}^{KBr}$ cm$^{-1}$: 1758 (C=O).

NMR(CD$_3$OD)δ: 1.74 (6H, s, >C(CH$_3$)$_2$); 1.50–4.18 (9H, m, piperidine protons); 7.18–7.60 (9H, m, aromatic protons).

EXAMPLE 50 p-Cyclohexylphenyl 1-amidino-4-piperidinecarboxylate hydrochloride

A mixture of 9.2 g of bis-(p-cyclohexylphenyl)sulfite, 4 g of 1-amidino-4-piperidinecarboxylic acid hydrochloride, 20 ml of dry dimethylformamide and 8 ml of dry pyridine was stirred at room temperature for 18 hours. The solvent was removed under reduced pressure, and the residue was treated with ethyl acetate to give crystals. The crystals were recrystallized from isopropanol-ether to obtain 2.9 g (yield: 40.8%) of p-cyclohexylphenyl 1-amidino-4-piperidinecarboxylate hydrochloride as colorless crystals having a melting point of 226° to 230° C.

IR $\nu_{max}^{KBr}$ cm$^{-1}$: 1760 (C=O).

NMR(CD$_3$OD)δ: 1.20–4.30 (20H, m, piperidine protons and cyclohexane protons); 7.16–7.64 (4H, m, aromatic protons).

EXAMPLE 51

2',4'-Dimethylphenyl 1-amidino-4-piperidinecarboxylate hydrochloride 8.4 g of bis-(2,4-dimethylphenyl)sulfite was dissolved in a solution of 36 ml of dry dimethylformamide and 18 ml of dry pyridine. To the solution was added 4.0 g of 1-amidino-4-piperidinecarboxylic acid hydrochloride, and the resulting mixture was stirred at room temperature for 4 hours. The solvent was removed under reduced pressure, and ether was added to the residue to obtain 5.8 g (yield: 96.7%) of 2',4'-dimethylphenyl 1-amidino-4-piperidinecarboxylate hydrochloride as colorless crystals having a melting point of 198° to 201° C.

The thus obtained crystals were further purified to give crystals having a melting point of 205° to 207° C.

IR $\nu_{max}^{KBr}$ cm$^{-1}$: 1745 (C=O).

NMR(CD$_3$OD)δ: 1.60–4.36 (9H, m, piperidine protons); 2.24 (3H, s, 4—C$\underline{H}_3$); 2.40 (3H, s, 2—C$\underline{H}_3$); 7.02–7.56 (3H, m, aromatic protons).

EXAMPLE 52 o-Allylphenyl 1-amidino-4-piperidinecarboxylate hydrochloride 2.4 g of bis-(o-allylphenyl)sulfite was dissolved in a solution of 10 ml of dry dimethylformamide and 5 ml of dry pyridine. To the solution was added 1.0 g of 1-amidino-4-piperidinecarboxylic acid hydrochloride, and the resulting mixture was allowed to stand at room temperature for 3 hours. The solvent was removed under reduced pressure, and ether was added to the residue to give crystals. The crystals were recrystallized from isopropanol-ether to obtain 950 mg (yield: 61.3%) of o-allylphenyl 1-amidino-4-piperidinecarboxylyate hydrochloride as colorless crystals having a melting point of 151° to 153° C.

IR $\nu_{max}^{KBr}$ cm$^{-1}$: 1740 (C=O).

NMR(CDCl$_3$)δ: 1.60–4.52 (11H, m, piperidine protons and C$\underline{H}_2$—Ph); 5.04–5.48 (2H, m, =C$\underline{H}_2$); 5.88–6.40 (1H, m, —C$\underline{H}$=); 7.24–8.08 (4H, m, aromatic protons).

EXAMPLE 53

Piperidine-4-acetic acid hydrochloride 15 g of 4-pyridyl acid hydrochloride was dissolved in 180 ml of water. To the solution was added 0.6 g of platinum dioxide, and the resulting mixture was subjected to catalytic reduction at an initial hydrogen pressure of 4.85 kg/cm$^2$. The reaction was terminated when 6.2 l of hydrogen gas was absorbed, and the catalyst was removed by filtration. The filtrate was evaporate to dryness under reduced pressure, and a small amount of ethanol was added to the residue. The solid in the mixture was crushed, and a large amount of ether was added to the mixture. Subsequent filtration of the resulting mixture gave 14.6 g of piperidine-4-acetic acid hydrochloride as a white solid having a melting point of 136° to 141° C.

IR $\nu_{max}^{KBr}$ cm$^{-1}$: 1710 (C=O).

NMR(CD$_3$OD)δ: 1.20–3.44 (11H, m).

EXAMPLE 54

1-Amidino-4-piperidineacetic acid

A mixture of 14 g of piperidine-4-acetic acid and 10.9 g of s-methylisothiourea ½ sulfate was added to 40 ml of a 4 N sodium hydroxide solution, and the mixture was stirred at room temperature for 20 hours. Methyl mercaptane formed was filtered to give crystals. The crystals were washed with ice-water and then with acetone and dried to obtain 12 g (yield: 83%) of 1-amidino-4-piperidineacetic acid as colorless powder having a melting point of over 310° C.

IR $\nu_{max}^{KBr}$ cm$^{-1}$: 1570, 1410.

EXAMPLE 55

1-Amidino-4-piperidineacetic acid hydrochloride 11.5 g of 1-amidino-4-piperidineacetic acid prepared in Example 54 was dissolved in 100 ml of a 1 N hydrochloric acid solution, and the solution was treated with activated charcoal and concentrated. Acetone was added to the residue to obtain 12.7 g (yield: 92%) of 1-amidino-4-piperidineacetic acid hydrochloride as colorless prisms having a melting point of 213° to 215.5° C.

IR $\nu_{max}^{KBr}$ cm$^{-1}$: 1720 (C=O).

EXAMPLE 56

Phenyl 1-amidino-4-piperidineacetate hydrochloride

A mixture of 2 g of 1-amidino-4-piperdineacetic acid hydrochloride and 3.2 g of diphenylsulfite was stirred at room temperature for 1.5 hours in a solution of 10 ml of dry dimethylformamide and 3 ml of dry pyridine. The solvent was removed under reduced pressure, and the residue was washed several times with ether to give crystals. The crystals were washed with ethyl acetate and then with ether to obtain 2.4 g (yield: 89%) of phenyl 1-amidino-4-piperidineacetate hydrochloride as colorless crystalline powder having a melting point of 131° to 136.5° C.

IR $\nu_{max}^{KBr}$ cm$^{-1}$: 1750 (C=O).

NMR(CD$_3$OD)δ: 1.20–4.10 (9H, m, piperidine protons); 2.60 (2H, d, J=6 Hz, C$\underline{H}_2$CO); 6.90–7.40 (5H, m, aromatic protons).

EXAMPLE 57

4'-Methoxyphenyl 1-amidino-4-piperidineacetate hydrochloride

A mixture of 2 g of 1-amidino-4-piperidineacetic acid hydrochloride and 4 g of bis-(p-methoxyphenyl)sulfite was stirred at room temperature for 4 hours in a solution of 10 ml of dry dimethylformamide and 3 ml of dry pyridine. The solvent was removed under reduced pressure, and the residue was washed several times with ether to give crystals. The crystals were washed with ethyl acetate and then with ether to obtain 2.9 g (quantitative) of 4'-methoxyphenyl 1-amidino-4-piperidineacetate hydrochloride as colorless crystalline powder having a melting point of 159° to 162° C.

IR $\nu_{max}^{KBr}$ cm$^{-1}$: 1740 (C=O).

NMR(CD$_3$OD)δ: 1.20–4.10 (9H, m, piperidine protons); 2.56 (2H, d, J=6 Hz, C$\underline{H}_2$CO); 3.80 (3H, s, OC$\underline{H}_3$); 6.90–7.20 (4H, m, aromatic protons).

EXAMPLE 58

4'-Chlorophenyl 1-amidino-4-piperidineacetate hydrochloride

A mixture of 2.0 g of 1-amidino-4-piperidineacetic acid hydrychloride and 4.6 g of bis-(p-chlorophenyl)-sulfite was stirred at room temperature for 2 hours in a solution of 10 ml of dry dimethylformamide and 3 ml of dry pyridine. The solvent was removed under reduced pressure, and 30 ml of ether was added to the residue, and the mixture was stimulated to give crystals. The crystals were washed with ethyl acetate and then with ether to obtain 2.7 g (yield: 90%) of 4'-chlorophenyl 1-amidino-4-piperidineacetate hydrochloride as colorless crystals having a melting point of 186.5° to 190.5° C.

IR $\nu_{max}^{KBr}$ cm$^{-1}$: 1760 (C=O).

NMR(CD$_3$OD)$\delta$: 1.10–4.10 (9H, m, piperidine protons); 2.60 (2H, d, J=6 Hz, CH$_2$CO); 7.04–7.60 (4H, m, aromatic protons).

EXAMPLE 59

4'-Methylphenyl 1-amidino-4-piperidineacetate hydrochloride

A mixture of 2.0 g of 1-amidino-4-piperidineacetic acid hydrochloride and 3.5 g of bis-(p-methylphenyl)-sulfite was stirred at room temperature for 2 hours in a solution of 10 ml of dry dimethylformamide and 3 ml of dry pyridine. The solvent was removed under reduced pressure, and 20 ml of ether was added to the residue. Thereafter, the mixture was stimulated to give crystals. The crystals were washed with ethyl acetate and then with ether to obtain 2.8 g (quantitative) of 4'-methylphenyl 1-amidino-4-piperidineacetate hydrochloride as colorless crystals having a melting point of 167° to 173° C.

IR $\nu_{max}^{KBr}$ cm$^{-1}$: 1750 (C=O).

NMR(CD$_3$OD)$\delta$: 1.20–4.10 (9H, m, piperidine protons); 2.38 (3H, s, CH$_3$); 2.62 (2H, d, J=6 Hz, CH$_2$CO); 6.90–7.40 (4H, m, aromatic protons).

EXAMPLE 60

2',4'-Dichlorophenyl 1-amidino-4-piperidineacetate hydrochloride

A mixture of 2.0 g of 1-amidino-4-piperidineacetic acid hydrochloride and 5.0 g of bis-(2,4-dichlorophenyl)sulfite prepared from 2,4-dichlorophenol and thionyl chloride was stirred at room temperature for 1 hour in a solution of 10 ml of dry dimethylformamide and 3 ml of dry pyridine. The solvent was removed under reduced pressure, and 20 ml of ether was added to the residue. The mixture was then stimulated to give crystals. The crystals were washed with ethyl acetate and then with ether and stirred for 10 minutes in 20 ml of acetone. The crystals were washed with ether to obtain 2.6 g (yield: 79%) of 2',4'-dichlorophenyl 1-amidino-4-piperidineacetate hydrochloride as colorless crystals having a melting point of 177.5° to 181.5° C.

IR $\nu_{max}^{KBr}$ cm$^{-1}$: 1765 (C=O).

NMR(CD$_3$OD)$\delta$: 1.20–4.10 (9H, m, piperidine protons); 2.70 (2H, d, J=6 Hz, CH$_2$CO); 7.20–7.70 (3H, m, aromatic protons).

EXAMPLE 61

4'-t-Butylphenyl 1-amidino-4-piperidineacetate hydrochloride

A mixture of 1.2 g of 1-amidino-4-piperidineacetic acid hydrochloride and 2.6 g of bis-(p-t-butylphenyl)-sulfite was stirred at room temperature for 2 hours in a solution of 5 ml of dry dimethylformamide and 2 ml of dry pyridine. The solvent was removed, and to the residue were added with stirring 20 ml of ethyl acetate and 100 ml of ether to give crystals. The crystals were recrystallized from methanol-ether to obtain 1.42 g (yield: 74%) of 4'-t-butylphenyl 1-amidino-4-piperidineacetate hydrochloride as colorless crystalline powder having a melting point of 183.5° to 187° C.

IR $\nu_{max}^{KBr}$ cm$^{-1}$: 1755 (C=O).

NMR(CD$_3$OD)$\delta$: 1.10–4.00 (9H, m, piperidine protons); 1.33 (9H, s, C(CH$_3$)$_3$; 2.56 (2H, d, J=6 Hz, CH$_2$CO); 6.84–7.44 (4H, m, aromatic protons).

EXAMPLE 62

1-Amidino-3-piperidinepropionic acid hydrochloride 15.7 g of piperidine-3-propionic acid was dissolved in 100 ml of a 1 N sodium hydroxide solution, and 14 g of s-methylisothiourea sulfate was added to the solution, and the resulting mixture was stirred slowly at room temperature for 20 hours. Methyl mercaptane formed was absorbed into a potassium manganate solution under reduced pressure. The crystals deposited were separated by filtration, washed with a small amount of cold water and dissolved in 117 ml of a 1 N hydrochloric acid solution. The solvent was removed, and the residue was dissolved in isopropyl alcohol. Isopropyl ether was added to the solution to give crystals which were then recrystallized from water to obtain 14 g (yield: 59%) of 1-amidino-3-piperidinepropionic acid hydrochloride as colorless crystals having a melting point of 220° to 222° C.

IR $\nu_{max}^{KBr}$ cm$^{-1}$: 1715 (C=O).

NMR (CD$_3$OD)$\delta$: 1.0–2.0 (7H, m, $\beta$-H$_2$, 3-H, 4- and 5-H$_2$); 2.36 (2H, t, J=6.4 Hz, $\alpha$-H$_2$); 2.64–3.84 (4H, m, 2-H$_2$ and 6-H$_2$).

EXAMPLE 63

Phenyl 1-amidino-3-piperidinepropionate hydrochloride 3 g of 1-amidino-3-piperidinepropionic acid hydrochloride was dissolved in a solution of 30 ml of dry dimethylformamide and 3 ml of dry pyridine. To the solution was add 4.5 g of diphenyl sulfite, and the resulting mixture was stirred at room temperature for 29 hours. The solvent was removed, and the residue was washed with dry ether and treated with ethyl acetate to give light brown powder. The powder was recrystallized from ethanol-ether to obtain 3.1 g (yield: 78%) of phenyl 1-amidino-3-piperidinepropionate hydrochloride as light brown powder having a melting point of 101° to 112° C.

IR $\nu_{max}^{KBr}$ cm$^{-1}$: 1760 (C=O).

NMR(CD$_3$OD)$\delta$: 1.0–2.1 (7H, m, $\beta$-H$_2$, 3-H, 4- and 5-H$_2$); 2.64 (2H, t, J=7.2 Hz, $\alpha$-H$_2$); 6.9–7.4 (5H, m, aromatic protons).

EXAMPLE 64

4'-Methoxyphenyl 1-amidino-3-piperidinepropionate hydrochloride 3 g of 1-amidino-3-piperidinepropionic acid hydrochloride, 5.6 g of bis-(p-methoxyphenyl)sulfite, 30 ml of dry dimethylformamide and 3 ml of dry pyridine were reacted for 17 hours by the same procedure as in Example 63. The solvent was removed, and the residue was washed with dry ether to give crystals. The crystals were recrystallized from methanol-ether to obtain 3.9 g (yield: 93%) of 4'-methoxyphenyl 1-amidino-3-piperidinepropionate hydrochloride as colorless needles having a melting point of 214° to 216° C.

IR $\nu_{max}^{KBr}$ cm$^{-1}$: 1760 (C=O).

NMR(CD$_3$OD)δ: 1.0–2.1 (7H, m, β-H$_2$, 3-H, 4- and 5-H$_2$); 2.6 (2H, t, J=7.2 Hz, α-H$_2$); 3.72 (3H, s, OCH$_3$); 6.83 (4H, s, aromatic proton).

EXAMPLE 65

4'-Chlorophenyl 1-amidino-3-piperidinepropionate hydrochloride 2 g of 1-amidino-3-piperidinepropionic acid hydrochloride, 10.3 g of bis-(p-chlorophenyl)sulfite, 20 ml of dry dimethylformamide and 5 ml of dry pyridine were reacted at room temperature for 1 hour, and the reaction mixture was treated by the same procedure as in Example 63. The product thus obtained was recrystallized from methanol-ether to obtain 2.4 g (yield: 82%) of 4'-chlorophenyl 1-amidino-3-piperidinepropionate hydrochloride as light brown needles having a melting point of 168° to 170° C.

IR $\nu_{max}^{KBr}$ cm$^{-1}$: 1750 (C=O).

NMR(CD$_3$OD)δ: 1.0–2.1 (7H, m, β-H$_2$, 3-H, 4- and 5-H$_2$); 2.67 (2H, t, J=6.8 Hz, α-H$_2$); 2.8–3.9 (4H, m, 2- and 6-H$_2$); 7.0–7.4 (4H, m, aromatic protons).

EXAMPLE 66

4'-Methylphenyl 1-amidino-3-piperidinepropionate hydrochloride 2.5 g of 1-amidino-3-piperidinepropionic acid hydrochloride, 9 g of bis-(p-methylphenyl)sulfite, 25 ml of dry dimethylformamide and 8 ml of dry pyridine were reacted at room temperature for 2 hours, and the reaction mixture was treated by the same procedure as in Example 63. The product thus obtained was recrystallized from ethanol-ether to obtain 3 g (yield: 87%) of 4'-methylphenyl 1-amidino-3-piperidinepropionate hydrochloride as colorless needles having a melting point of 189° to 192° C.

IR $\nu_{max}^{KBr}$ cm$^{-1}$: 1750 (C=O).

NMR(CD$_3$OD)δ: 1.1–2.1 (7H, m, β-H$_2$, 3-H, 4- and 5-H$_2$); 2.36 (3H, s, —CH$_3$); 2.70 (2H, d, J=6.8 Hz, α-H$_2$); 2.80–4.0 (4H, m, 2- and 6-H$_2$); 7.0–7.4 (4H, m, aromatic protons).

EXAMPLE 67

2',4'-Dichlorophenyl 1-amidino-3-piperidinepropionate hydrochloride 2 g of 1-amidino-3-piperidinepropionic acid hydrochloride was suspended in 10 ml of dry dimethylformamide. To the suspension were added with cooling on a water bath 4.8 g of bis-(2,4-dichlorophenyl)sulfite and 3 ml of dry pyridine, and the resulting mixture was stirred at room temperature for 3 hours. The solvent was removed under reduced pressure, and ether was added to the residue. Thereafter, the mixture was stimulated to give crystals. The crystals were washed with ethyl acetate and then with ether and recrystallized from isopropanol to obtain 2.2 g (yield: 68%) of 2',4'-dichlorophenyl 1-amidino-3-piperidinepropionate hydrochloride as colorless crystals having a melting point of 170.5° to 174° C.

IR $\nu_{max}^{KBr}$ cm$^{-1}$: 1770 (C=O).

NMR(CD$_3$OD)δ: 1.10–4.00 (13H, m, piperidine protons and CH$_2$CH$_2$CO); 7.20–7.70 (3H, m, aromatic protons).

EXAMPLE 68

4'-t-Butylphenyl 1-amidino-3-piperidinepropionate hydrochloride 1 g of 1-amidino-3-piperidinepropionic acid hydrochloride was suspended in a solution of 10 ml of dry dimethylformamide and 5 ml of dry pyridine. To the suspension was added 1.76 g of bis-(p-t-butylphenyl)sulfite, and the resulting mixture was stirred at room temperature for 2.5 hours. The solvent was removed under reduced pressure to give crystals. The crystals were washed with dry ether and recrystallized three times from ethanol-ether to obtain 1 g (yield: 64%) of 4'-t-butylphenyl 1-amidino-3-piperidinepropionate hydrochloride as colorless needles having a melting point of 212° to 214° C.

IR $\nu_{max}^{KBr}$ cm$^{-1}$: 1740 (C=O).

NMR(CD$_3$OD)δ: 1.0–2.1 (7H, m, β-H$_2$, 3-H, 4- and 5-H$_2$); 1.35 (9H, s, C(CH$_3$)$_3$); 2.5–4.1 (6H, m, α-, 2- and 6-H$_2$); 7.0–7.7 (4H, m, aromatic protons).

EXAMPLE 69

1-Amidino-3-piperidinebutyric acid hydrochloride (1) 20 g of 3-pyridylbutyric acid was suspended in 250 ml of water, and the suspension was shaken in a stream of hydrogen (5 to 6 kg/cm$^2$) in the presence of 1 g of platinum dioxide. When the absorption of hydrogen was terminated, the catalyst was removed by filtration. The filtrate was washed with water, and the solvent was removed to give powder. The powder was recrystallized from ethanol to obtain 19 g of 3-piperidinebutyric acid as colorless needles having a melting point of 208° to 210° C.

IR $\nu_{max}^{KBr}$ cm$^{-1}$: 1760 (C=O).

NMR(CD$_3$OD)δ: 1.0–2.0 (9H, m, β- and γ-H$_2$, 3-H, 4-H$_2$ and 5-H$_2$); 2.13 (2H, t, J=6.4 Hz, α-H$_2$); 2.4–3.46 (4H, m, 2-H$_2$ and 6-H$_2$).

(2) 20 g of 3-piperidinebutyric acid prepared in item (1) above was dissolved in 117 ml of a 1 N sodium hydroxide solution. To the solution was added 16.3 g of S-methylisothiourea sulfate, and the resulting mixture was stirred slowly at room temperature for 20 hours. Methyl mercaptane formed was absorbed into a potassium manganate solution under reduced pressure. The crystals deposited were separated by filtration, washed with a small amount of cold water and dissolved in 117 ml of a 1 N hydrochloric acid solution. The solvent was removed, and the residue was dissolved in isopropyl alcohol, and isopropyl ether was then added to the solution to obtain 18.3 g (yield: 63%) of 1-amidino-3-piperidinebutyric acid hydrochloride as colorless needles having a melting point of 112° to 115° C.

IR $\nu_{max}^{KBr}$ cm$^{-1}$: 1700 (C=O).

NMR(CD$_3$OD)δ: 1.0–2.0 (9H, m, β- and γ-H$_2$, 3-H, 4-H$_2$ and 5-H$_2$); 2.24 (2H, t, J=6.4 Hz, α-H$_2$); 2.52–3.76 (4H, m, 2-H$_2$ and 6-H$_2$).

EXAMPLE 70

Phenyl 1-amidino-3-piperidinebutyrate hydrochloride 3 g of 1-amidino-3-piperidinebutyric acid hydrochloride, 4.2 g of diphenylsulfite, 30 ml of dry dimethylformamide and 3 ml of dry pyridine were reacted for 19.5 hours in accordance with the procedure employed in Example 63. The solvent was removed, and the residue was washed with dry ether to obtain 3.9 g of phenyl 1-amidino-3-piperidinebutyrate hydrochloride as an oil.

IR $\nu_{max}^{neat}$ cm$^{-1}$: 1760 (C=O).

NMR(CD$_3$OD)$\delta$: 1.0–2.0 (9H, m, $\beta$-H$_2$, $\gamma$-H$_2$, 3-H, 4-H$_2$ and 5-H$_2$); 2.48 (2H, t, J=6.4 Hz, $\alpha$-H$_2$); 2.5–3.8 (4H, m, 2- and 6-H$_2$); 6.6–7.3 (5H, m, aromatic protons).

EXAMPLE 71

4'-Methoxyphenyl 1-amidino-3-piperidinebutyrate hydrochloride 3 g of 1-amidino-3-piperidinebutyric acid hydrochloride and 5.3 g of bis-(p-methoxyphenyl)sulfite were reacted for 17 hours in accordance with the procedure employed in Example 63. The solvent was removed, and the residue was washed with dry ether and dissolved in chloroform. Ethyl acetate was added to the solution to obtain 2.9 g (yield: 68%) of 4'-methoxyphenyl 1-amidino-3-piperidinebutyrate hydrochloride as colorless powder having a melting point of 122° to 130° C.

IR $\nu_{max}^{KBr}$ cm$^{-1}$: 1760 (C=O).

NMR(CD$_3$OD)$\delta$: 1.0–2.0 (9H, m, $\beta$-, $\gamma$-H$_2$, 3-H, 4- and 5-H$_2$); 2.5 (2H, t, J=6.4 Hz, $\alpha$-H$_2$); 3.68 (3H, s, OCH$_3$); 6.79 (4H, s, aromatic proton).

EXAMPLE 72

4'-chlorophenyl 1-amidino-3-piperidinebutyrate hydrochloride 3 g of 1-amidino-3-piperidinebutyric acid hydrochloride, 7.3 g of bis-(p-chlorophenyl)sulfite, 30 ml of dry dimethylformamide and 10 ml of dry pyridine were reacted and treated in accordance with the procedure employed in Example 63 to obtain 3 g (yield: 69%) of 4'-chlorophenyl 1-amidino-3-piperidinebutyrate hydrochloride as light brown needles having a melting point of 155° to 157° C.

IR $\nu_{max}^{KBr}$ cm$^{-1}$: 1755 (C=O).

NMR(CD$_3$OD)$\delta$: 1.1–2.1 (9H, m, $\beta$-, $\gamma$-H$_2$, 3-H, 4- and 5-H$_2$); 2.66 (2H, t, J=6.8 Hz, $\alpha$-H$_2$); 2.8–4.0 (4H, m, 2- and 6-H$_2$); 7.2–7.6 (4H, m, aromatic protons).

EXAMPLE 73

2',4'-Dichlorophenyl 1-amidino-3-piperidinebutyrate hydrochloride 2 g of 1-amidino-3-piperidinebutyric acid hydrochlorice was suspended in 10 ml of dry dimethylformamide. To the suspension were added 4.5 g of bis-(2,4-dichlorophenyl)sulfite and 3 ml of dry pyridine, and the resulting mixture was stirred at room temperature for 2 hours. The solvent was removed under reduced pressure, and the residue was washed three times with 20 ml of ether and then stimulated to give crystals. The crystals were washed with ethyl acetate and then with ether to obtain 2.4 g (yield: 76%) of 2',4'-dichlorophenyl 1-amidino-3-piperidinebutyrate hydrochloride as colorless crystals having a melting point of 138° to 141° C.

IR $\nu_{max}^{KBr}$ cm$^{-1}$: 1780 (C=O).

NMR(CD$_3$OD)$\delta$: 1.20–4.00 (15H, m, piperidine protons and C$\underline{H}_2$C$\underline{H}_2$CO); 7.20–7.70 (3H, m, aromatic protons).

EXAMPLE 74

4'-Methylphenyl 1-amidino-3-piperidinebutyrate hydrochloride

A mixture of 3 g of 1-amidino-3-piperidinebutyric acid hydrochloride, 4.7 g of bis-(p-methylphenyl)sulfite; 15 ml of dry dimethylformamide and 5 ml of dry pyridine was stirred at room temperature for 2 hours. The solvent was removed, and the residue was treated with ethyl acetate to give a solid substance. The substance was washed several times with ethyl acetate and then with ether and dried to obtain 3.7 g (yield: 90%) of 4'-methylphenyl 1-amidino-3-piperidinebutyrate hydrochloride as colorless crystals having a melting point of 138° to 140° C.

IR $\nu_{max}^{KBr}$ cm$^{-1}$: 1750 (C=O).

NMR(CD$_3$OD)$\delta$: 1.10–2.10 (9H, m, $\beta$-, $\gamma$-H$_2$, 3-H, 4- and 5-H$_2$); 2.52 (3H, s, CH$_3$); 2.60 (2H, t, J=8 Hz, $\alpha$-H$_2$); 2.76–4.00 (4H, m, 2- and 6-H$_2$); 6.90–7.40 (4H, m, aromatic protons).

EXAMPLE 75

4'-t-Butylphenyl 1-amidino-3-piperidinebutyrate hydrochloride

A mixture of 2 g of 1-amidino-3-piperidinebutyric acid hydrochloride, 4.16 g of bis-(p-t-butylphenyl)sulfite, 20 ml of dry dimethylformamide and 10 ml of dry pyridine was stirred at room temperature for 16 hours. The solvent was removed under reduced pressure, and the residue was washed with dry ether and then dissolved in isopropyl alcohol. Water was added to the solution, and the mixture was cooled to give colorless crystals. The crystals were washed with cold water and dried to obtain 1.9 g (yield: 62%) of 4'-t-butylphenyl 1-amidino-3-piperidinebutyrate hydrochloride as colorless crystals having a melting point of 164° to 169° C.

IR $\nu_{max}^{KBr}$ cm$^{-1}$: 1755 (C=O).

NMR(CD$_3$OD)$\delta$: 1.0–2.1 (9H, m, 3-H, $\beta$-, $\gamma$-, 4- and 5-H$_2$); 1.32 (9H, s, C(CH$_3$)$_3$); 2.3–3.9 (6H, m, $\alpha$-, 2- and 6-H$_2$); 6.96–7.5 (4H, m, aromatic protons).

EXAMPLE 76

1-Amidino-4-piperidinebutyric acid hydrochloride

A mixture of 13.0 g of o-methylisourea sulfate and 15.7 g of 4-piperidinebutyric acid hydrochloride was dissolved with stirring and ice-cooling in 60 ml of a 4 N sodium hydroxide solution. To the solution was added 20 ml of water, and the resulting mixture was stirred at room temperature for 64 hours. The crystals obtained were washed with 300 ml of ice-water and dehydrated with acetone and further washed with ether. The crystals were dissolved in 90 ml of a 1 N hydrochloric acid solution, and the solution was dried under reduced pressure. The residue was washed with acetone and then with ether and air-dried to obtain 16.3 g (yield: 86.7%) of 1-amidino-4-piperidinebutyrate hydrochloride as colorless crystals having a melting point of 178° to 180° C.

IR $\nu_{max}^{KBr}$ cm$^{-1}$: 1624, 1726.

NMR(CD$_3$OD)$\delta$: 0.96–1.94 (9H, m, $\beta$-H$_2$, $\gamma$-H$_2$, 4-H and 5-H$_2$); 2.27 (2H, t, $\alpha$-H$_2$); 2.86–3.98 (4H, m, 2-H$_2$, 6-H$_2$).

EXAMPLE 77

Phenyl 1-amidino-4-piperidinebutyrate hydrochloride

A mixture of 2.5 g of 1-amidino-4-piperidinebutyric acid hydrochloride and 2.9 g of diphenylsulfite was stirred at room temperature for 3 hours in a solution of 14 ml of dry dimethylformamide and 7 ml of dry pyridine. The solvent was removed under reduced pressure. Dry ether was added to the residue, and the mixture was stirred overnight to give crystals. The crystals were recrystallized from methanol-ether to obtain 2.3 g (yield: 70%) of phenyl 1-amidino-4-piperidinebutyrate hydrochloride as pale yellow crystals having a melting point of 166° to 167° C.

IR $\nu_{max}^{KBr}$ cm$^{-1}$: 1612, 1754.

NMR(CD$_3$OD)δ: 0.97-1.96 (9H, m, β-H$_2$, γ-H$_2$, 3-H$_2$, 4-H and 5-H$_2$); 2.55 (2H, t, α-H$_2$); 2.84-3.96 (4H, m, 2-H$_2$, 6-H$_2$);

5 ml of dry pyridine was added to a mixture of 3 g of 1-amidino-4-piperidinebutyric acid hydrochloride, 15 ml of dry dimethylformamide and 4.4 g of bis-(p-methylphenyl)sulfite, and the resulting mixture was stirred at room temperature for 3 hours. The solvent was removed under reduced pressure, and ethyl acetate was added to the residue to give crystals. The crystals were washed with ethyl acetate and then with ether and recrystallized from methanol-ether to obtain 3.8 g (yield: 92.7%) of 4'-methylphenyl 1-amidino-4-piperidinebutyrate hydrochloride as yellow needles having a melting point of 160° to 163° C.

IR $\nu_{max}^{KBr}$ cm$^{-1}$: 1760.

NMR(CD$_3$OD)δ: 1.00-2.00 (9H, m, β-H$_2$, γ-H$_2$, 3-H$_2$, 4-H and 5-H$_2$); 2.30 (3H, s, CH$_3$); 2.52 (2H, t, J=7 Hz, CH$_2$CO); 2.80-4.00 (4H, m, 2-H$_2$, 6-H$_2$); 6.80-7.20 (4H, m, aromatic protons).

EXAMPLE 79

4'-Methoxyphenyl 1-amidino-4-piperidinebutyrate hydrochloride 3 g of 1-amidino-4-piperidinebutyric acid hydrochloride was dissolved in a solution of 15 ml of dry dimethylformamide and 5 ml of dry pyridine. 5.3 g of bis-(p-methoxyphenyl)sulfite was added to the solution, and the resulting mixture was stirred at room temperature for 5 hours. The reaction mixture was treated by the same procedure as in Example 63. The crystals obtained were recrystallized from methanol-ether to obtain 4 g (yield: 93.6%) of 4'-methoxyphenyl 1-amidino-4-piperidinebutyrate hyrochloride as colorless needles having a melting point of 173° to 176° C.

IR $\nu_{max}^{KBr}$ cm$^{-1}$: 1760 (C=O).

NMR(CD$_3$OD)δ: 0.8-2.0 (9H, m, β-H$_2$, γ-H$_2$, 3-H$_2$, 4-H and 5-H$_2$); 2.24 (2H, t, J=6.8 Hz, α-H$_2$); 2.80-3.95 (4H, m, 2-H$_2$, 6-H$_2$); 3.71 (3H, s, O—CH$_3$); 6.82 (4H, s, aromatic proton).

EXAMPLE 80

4'-Chlorophenyl 1-amidino-4-piperidinebutyrate hydrochloride

A mixture of 3 g of 1-amidino-4-piperidinebutyric acid hydrochloride, 5.1 g of bis-(p-chlorophenyl)sulfite, 15 ml of dry dimethylformamide and 5 ml of dry pyridine was stirred at room temperature for 2.5 hours. The reaction mixture was treated by the same procedure as in Example 65. The crystals obtained were recrystallized from methanol-ether to obtain 2.9 g (yield: 67%) of 4'-chlorophenyl 1-amidino-4-piperidinebutyrate hydrochloride as colorless needles having a melting point of 166° to 168° C.

IR $\nu_{max}^{KBr}$ cm$^{-1}$: 1765.

NMR(CD$_3$OD)δ: 0.9-2.9 (9H, m, β-H$_2$, γ-H$_2$, 3-H$_2$, 4-H and 5-H$_2$); 2.52 (2H, t, J=7.4 Hz, α-H$_2$); 2.8-3.9 (4H, m, 2-H$_2$ and 6-H$_2$); 6.96-7.48 (4H, m, aromatic protons).

EXAMPLE 81

4'-t-Butylphenyl 1-amidino-4-piperidinebutyrate hydrochloride

A mixture of 2.5 g of 1-amidino-4-piperidinebutyric acid hydrochloride and 4.3 g of bis-(p-t-butylphenyl)sulfite was stirred at room temperature for 6 hours in a solution of 14 ml of dry dimethylformamide and 7 ml of dry pyridine. The solvent was removed under reduced pressure, and dry ether was added to the residue to give crystals. The crystals were recrystallized from ethanol-ether acetate to obtain 2.2 g (yield: 58%) of 4'-t-butylphenyl 1-amidino-4-piperidinebutyrate hydrochloride as colorless crystals having a melting point of 147° to 149° C.

IR $\nu_{max}^{KBr}$ cm$^{-1}$: 1621, 1642, 1758.

NMR(CD$_3$OD)δ: 0.97-1.96 (9H, m, β-H$_2$, γ-H$_2$, 3-H$_2$, 4-H and 5-H$_2$); 1.32 (9H, s, —C(CH$_3$)$_3$); 2.54 (2H, t, α-H$_2$); 2.81-3.96 (4H, m, 2-H$_2$, 6-H$_2$); 6.83-7.42 (4H, m, aromatic protons).

EXAMPLE 82

2',4'-Dichlorophenyl 1-amidino-4-piperidinebutyrate hydrochloride 18 ml of dry pyridine was added on an ice bath to a mixture of 5 g of 1-amidino-4-piperidinebutyric acid hydrochloride, 25 ml of dry dimethylformamide and 10.7 g of bis-(2,4-dichlorophenyl)sulfite, and the resulting mixture was stirred at room temperature for 1 hour. The solvent was removed under reduced pressure, and the residue was washed several times with ether and treated with ethyl acetate to give crystals. The crystlas were washed in turn with ethyl acetate, ether and acetone and then recrystallized from isopropanol-ether to obtain 4.2 g (yield: 49%) of 2',4'-dichlorophenyl 1-amidino-4-piperidinebutyrate hydrochloride as yellow powder having a melting point of 122° to 124° C.

IR $\nu_{max}^{KBr}$ cm$^{-1}$: 1770.

NMR(CD$_3$OD)δ: 1.00-2.00 (9H, m, β-H$_2$, γ-H$_2$, 3-H$_2$, 4-H and 5-H$_2$); 2.60 (2H, t, J=7 Hz, α-H$_2$); 2.80-4.00 (4H, m, 2-H$_2$, 6-H$_2$); 7.00-7.50 (3H, m, aromatic protons).

EXAMPLE 83

2'-Cinnamoylphenyl 1-amidino-4-piperidinepropionate hydrochloride

A mixture of 5 g of 1-amidino-4-piperidinepropionic acid hydrochloride, 4.8 g of 2'-hydroxychalcone, 4.4 g of N,N'-dicyclohexylcarbodiimide and 30 ml of dry pyridine was stirred at room temperature for 46 hours. After removal of any insoluble materials, the solvent was removed under reduced pressure to give a yellow oil. The oil was washed with ethyl acetate to give a gummy substance. The substance was dissolved in water. Thereafter, diethyl ether was added to the mixture, and the resulting mixture was stirred and allowed to stand overnight in cold conditions. The solid obtained was washed several times with diethyl ether and then with water to obtain 1.8 g of 2'-cinnamoylphenyl 1- amidino-4-piperidinepropionate hydrochloride as white powder having a melting point of 103° to 105° C.

IR $\nu_{max}^{KBr}$ cm$^{-1}$: 1765, 1660 (C=O).

NMR(CD$_3$OD)δ: 0.9–4.0

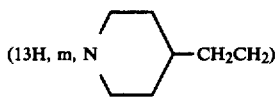

6.6–7.6 (11H, m, —CH=CH— and aromatic protons).

EXAMPLE 84

2'-(β-Phenylcarbonyl)ethenylphenyl 1-amidino-4-piperidinepropionate hydrochloride A mixture of 5 g of 1-amidino-4-piperidinepropionic acid hydrochloride, 4.8 g of 2-hydroxychalcone, 4.4 g of dicyclohexylcarbodiimide and 30 ml of dry pyridine was stirred at room temperature for 46 hours. After removal of any insoluble materials by filtration, the solvent was removed under reduced pressure to give an oily substance. The substance was washed with ethyl acetate to give a gummy substance which was then dissolved in water. To this mixture was added ethyl acetate, and the resulting mixture was stirred and allowed to stand overnight in cold conditions. The solid substance obtained was washed several times with diethyl ether and then with water to obtain 3 g (yield: 32.3%) of 2'-(β-phenylcarbonyl)ethenylphenyl 1-amidino-4-piperidinepropionate hydrochloride as yellow needles having a melting point of 85° C.

IR $\nu_{max}^{KBr}$ cm$^{-1}$: 1755, 1660 (C=O).

NMR(CD$_3$OD)δ: 1.0–3.66

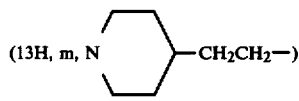

6.5–8.0 (11H, m, —CH=CH— and aromatic protons).

EXAMPLE 85

4'-(β-Diphenylmethyloxycarbonyl)ethenylphenyl 1-amidino-4-piperidinepropionate hydrochloride 9.9 g of p-coumaric acid diphenylmethyl ester prepared from p-coumaric acid and diphenyldiazomethane was dissolved in 70 ml of dry pyridine. To the solution were added 6.4 g of 1-amidino-4-piperidinepropionic acid hydrochloride and 5.6 g of N,N-dicyclohexylcarbodiimide, and the resulting mixture was stirred for 3 days at room temperature and overnight at 45° C. Thereafter, 1.4 g of N,N-dicyclohexylcarbodiimide was added to the reaction mixture, and the mixture was stirred overnight at 45° C. After cooling, the crystals separated by filtration were washed with cold pyridine several times, then with ethyl acetate and finally with ether and then air-dried at room temperature. The crystals were stirred in 100 ml of dichloromethane, and any insoluble materials were removed by filtration. The solvent was removed under reduced pressure, and ether was added to the residue to give crystals. The crystals were washed with ethyl acetate and then with ether and air-dried to obtain 6.4 g (yield: 43%) of 4'-(β-diphenylmethyloxycarbonyl)ethenylphenyl 1-amidino-4-piperidinepropionate hydrochloride as colorless crystals having a melting point of 135° to 138° C.

IR $\nu_{max}^{KBr}$ cm$^{-1}$: 1710, 1760 (C=O)

NMR(CDCl$_3$)δ: 1.10–4.34 (13H, m, piperidine, —(CH$_2$)$_2$—)

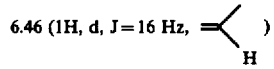
6.46 (1H, d, J=16 Hz,

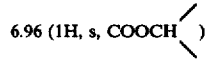
6.96 (1H, s, COOCH )

6.80–7.70 (14H, m, aromatic protons)

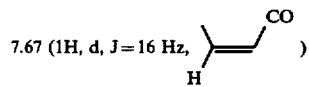
7.67 (1H, d, J=16 Hz,

EXAMPLE 86

4'-(β-Carboxy)ethenylphenyl 1-amidino-4-piperidinepropionate hydrochloride 2.6 g of 4'-(β-diphenylmethyloxycarbonyl)ethenylphenyl 1-amidino-4-piperidinepropionate hydrochloride was dissolved in 50 ml of formic acid, and the solution was stirred at 40° C. for 2 hours. The solvent was removed under reduced pressure, and ether was added to the residue to give crystals. The crystals were washed several times with ether to obtain 1.7 g (yield: 94%) of 4'-(β-carboxy)ethenylphenyl 1-amidino-4-piperidinepropionate hydrochloride as colorless crystals having a melting point of 249° to 250° C.

IR $\nu_{max}^{KBr}$ cm$^{-1}$:

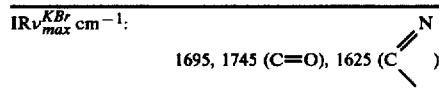
1695, 1745 (C=O), 1625 (C )

NMR(CD$_3$OD)δ: 1.00–4.34 (13H, m, piperidine, —(CH$_2$)$_2$—)

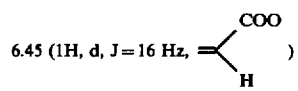
6.45 (1H, d, J=16 Hz,

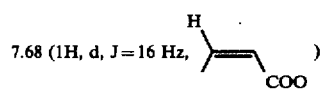
7.68 (1H, d, J=16 Hz, 7.04–7.82 (4H, m, aromatic protons)

EXAMPLE 87

2'-Methoxy-4'-(β-diphenylmethoxycarbonyl)ethenylphenyl 1-amidino-4-piperidinepropionate hydrochloride A mixture of 6 g of 1-amidino-4-piperidinepropionate hydrochloride, 10 g of 4-hydroxy-3-methoxycinnamic acid diphenylmethyl ester, 5.6 g of N,N'-dicyclohexylcarbodiimide and 50 ml of dry dimethylformamide was stirred at room temperature for 66 hours and at 60° C. for another 1 hour. After removal of any insoluble materials by filtration, the solvent was removed to give an oily substance. The substance was treated with ethyl acetate and diethyl ether to give a solid. Water was added to the solid to deposit crystals. The crystals were washed with acetone and then with diethyl ether and recrystallized from methanol-diethyl ether to obtain 2.8 g (yield: 19.4%) of 2'-methoxy-4'-(β-diphenylmethoxycarbonyl)ethenylphenyl 1-amidino-4-piperidinepropionate hydrochloride as white powder having a melting point of 118° to 120° C.

IR $\nu_{max}^{KBr}$ cm$^{-1}$: 1760, 1720 (C=O).

NMR(CD$_3$OD)δ: 0.9–4.06

(13H, m, —N◯—CH$_2$CH$_2$—)

3.61 (3H, s, —OCH$_3$); 6.50 (1H, d, J=16 Hz, =CH—COO); 6.75 (1H, s, COOCH<); 6.94–7.30 (13H, m, aromatic protons); 7.54 (1H, d, J=16 Hz, —CH=).

EXAMPLE 88

4'-(β-Hydroxycarbonylethenyl)-2'-methoxyphenyl 1-amidino-4-piperidinepropionate hydrochloride A solution of 1.6 g of 2'-methoxy-4'-(β-diphenylmethoxycarbonyl)ethylphenyl 1-amidino-4-piperidinepropionate hydrochloride and 30 ml of formic acid was stirred at 50° C. for 1 hour. After concentration and cooling of the reaction mixture, a sufficient amount of diethyl ether was added to the residue. The mixture was allowed to stand overnight in cold conditions to give crystals. The crystals were washed with diethyl ether and air-dried to obtain 1.1 g of 4'-(β-hydroxycarbonylethenyl)-2'-methoxyphenyl 1-amidino-4-piperidinepropionate hydrochloride as white powder having a melting point of 198° to 200° C.

IR $\nu_{max}^{KBr}$ cm$^{-1}$: 1740, 1720 (C=O).

NMR(CF$_3$COOH)δ: 1.00–4.10

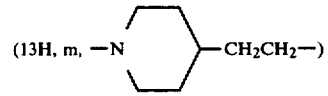

(13H, m, —N◯—CH$_2$CH$_2$—)

3.81 (3H, s, —OCH$_3$); 6.47 (1H, d, J=16 Hz, =CHCOO); 7.78 (1H, d, J=16 Hz, —CH=); 8.15–8.50 (3H, m, aromatic protons).

EXAMPLE 89

4'-Allyl-2'-methoxyphenyl 1-amidino-4-piperidinepropionate hydrochloride

A mixture of 2.0 g of 1-amidino-4-piperidinepropionic acid hydrochloride and 1.4 g of eugenol was dissolved in 30 ml of dry pyridine. To the solution was added 1.75 g of N,N'-dicyclohexylcarbodiimide, and the resulting mixture was stirred at room temperature for 5 days. Subsequently, 1.0 g of N,N'-dicyclohexylcarbodiimide was added to the reaction mixture, and the resulting mixture was stirred overnight at 40° C. After removal of any insoluble materials by filtration, the filtrate was concentrated under reduced pressure. 50 ml of water was added to the residue, and the solution was allowed to stand for 2 days to give crystals. The crystals were washed with a small amount of water and then with ether and dried to obtain 1.35 g (yield: 42%) of 4'-allyl-2'-methoxyphenyl 1-amidino-4-piperidinepropionate hydrochloride as colorless crystals having a melting point of 83° to 86° C.

IR $\nu_{max}^{KBr}$ cm$^{-1}$:

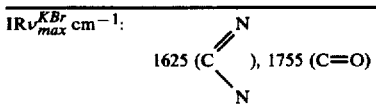

1625 (C⟨N/N⟩), 1755 (C=O)

NMR(CDCl$_3$)δ:

1.00–4.34 (13H, m, HN◯—CH$_2$CH$_2$—)

3.36 (2H, d, CH$_2$⌇)

3.80 (3H, s, —O—CH$_3$)
4.92–5.24 (2H, m, —CH$_2$—CH=CH$_2$)
5.72–6.16 (1H, m, —CH$_2$—CH=CH$_2$)
6.64–7.04 (3H, m, aromatic protons)

EXAMPLE 90

1-Amidino-3-piperidinecarboxylic acid hydrochloride 22 g of s-methylisothiourea ½ sulfuric acid was added with ice-cooling to a solution of 6.5 g of sodium hydroxide and 120 ml of water. To the mixture was added 20 g of nipecotic acid, and the resulting mixture was stirred at room temperature for 40 hours. The reaction mixture was filtered to give crystals. The crystals were washed in turn with cold water, acetone and ether. Thereafter, the crystals were dissolved in 110 ml of 1 N hydrochloride, and the resulting solution was stirred at room temperature for 45 minutes. After removal of any insoluble materials by filtration, the filtrate was concentrated under reduced pressure to give white powder, and the powder was dissolved in methanol. Ether was added to the solution to give crystals which were then washed with ether to obtain 10 g of 1-amidino-3-piperidinecarboxylic acid hydrochloride as white powder having a melting point of 234° to 236° C.

IR $\nu_{max}^{KBr}$ cm$^{-1}$: 1710 (C=O).

NMR(CD$_3$OD)δ: 1.40–3.80 (9H, m, piperidine protons).

EXAMPLE 91

Phenyl 1-amidino-3-piperidinecarboxylate hydrochloride

A mixture of 3 g of 1-amidino-3-piperidinecarboxylic acid hydrochloride, 1.4 g of phenol, 3 g of dicyclohexylcarbodiimide and 40 ml of dry pyridine was stirred at room temperature for 2 days. After removal of any insoluble materials, the solvent was removed under reduced pressure to give a light yellow oil. The oil was washed twice with ethyl acetate to give white powder. The powder was washed with dry ether and dried under reduced pressure to obtain 3 g of phenyl 1-amidino-3-piperidinecarboxylate hydrochloride as hygroscopic white powder having a melting point of 54° to 60° C.

IR $\nu_{max}^{KBr}$ cm$^{-1}$: 1750 (C=O).

NMR(CD$_3$OD)δ: 1.40–4.00 (9H, m, piperidine protons); 6.80–7.40 (5H, m, aromatic protons).

EXAMPLE 92

4'-Methoxyphenyl 1-amidino-3-piperidinecarboxylate hydrochloride

A mixture of 2 g of 1-amidino-3-piperidinecarboxylic acid hydrochloride, 1.2 g of p-methoxyphenol, 2 g of dicyclohexylcarbodiimide and 30 ml of dry pyridine was stirred at room temperature for 2 days. After removal of any insoluble materials, the solvent was removed under reduced pressure to give an oily substance. The substance was washed with ice-cooling with ethyl acetate to give a solid substance. The solid was dissolved in methanol, and any insoluble materials were removed by filtration. Ether was added to the solution, and the resulting mixture was allowed to stand overnight in cold conditions. The crystals obtained were washed with ether and then dried to obtain 2.5 g (yield: 83%) of 4'-methoxyphenyl 1-amidino-3-piperidinecarboxylate hydrochloride as light orange powder having a melting point of 140° to 143° C.

IR $\nu_{max}^{KBr}$ cm$^{-1}$: 1740 (C=O).

NMR(CD$_3$OD)$\delta$: 1.50–4.00 (9H, m, piperidine protons); 3.70 (3H, s, OC$\underline{H}_3$); 6.50–7.00 (4H, m, aromatic protons).

EXAMPLE 93

4'-Methylphenyl 1-amidino-3-piperidinecarboxylate hydrochloride

A mixture of 3 g of 1-amidino-3-piperidinecarboxylic acid, 5.6 g of bis-(p-methylphenyl)sulfite, 15 ml of dry dimethylformamide and 5 ml of dry pyridine was stirred at room temperature for 2.5 hours. The solvent was removed under reduced pressure. The residue was washed with ethyl acetate and then with ether several times and dried under reduced pressure to obtain 3.2 g (yield: 74%) of 4'-methylphenyl 1-amidino-3-piperidinecarboxylate hydrochloride as hygroscopic pale orange powder having a melting point of 103° to 110° C. The powder was further washed with ether to give powder having a melting point of 138° to 140° C.

IR $\nu_{max}^{KBr}$ cm$^{-1}$: 1760 (C=O).

NMR(CD$_3$OD)$\delta$: 1.50–4.00 (9H, m, piperidine protons); 2.32 (3H, s, C$\underline{H}_3$); 6.90–7.40 (4H, m, aromatic protons).

EXAMPLE 94

4'-Chlorophenyl 1-amidino-3-piperidinecarboxylate hydrochloride

The same procedure as in Example 93 was followed using 3 g of 1-amidino-3-piperidinecarboxylic acid hydrochloride, 6.6 g of bis-(p-chlorophenyl)sulfite, 15 ml of dry dimethylformamide and 5 ml of dry pyridine, thereby obtaining 2.9 g (yield: 64%) of 4'-chlorophenyl 1-amidino-3-piperidinecarboxylate hydrochloride as light orange powder having a melting point of 160° to 163° C.

IR $\nu_{max}^{KBr}$ cm$^{-1}$: 1760 (C=O).

NMR(CD$_3$OD)$\delta$: 1.60–4.00 (9H, m, piperidine protons); 7.08–7.50 (4H, m, aromatic protons).

EXAMPLE 95

2',4'-Dichlorophenyl 1-amidino-3-piperidinecarboxylate hydrochloride

The same procedure as in Example 93 was followed using 3.1 g of 1-amidino-3-piperidinecarboxylic acid hydrochloride, 8.4 g of bis-(2,4-dichlorophenyl)sulfite, 15 ml of dry dimethylformamide and 5 ml of dry pyridine, thereby obtaining 1.8 g (yield: 34%) of 2',4'-dichlorophenyl 1-amidino-3-piperidinecarboxylate hydrochloride as white powder having a melting point of 164° to 166° C.

IR $\nu_{max}^{KBr}$ cm$^{-1}$: 1760 (C=O).

NMR(CD$_3$OD)$\delta$: 1.50–4.00 (9H, m, piperidine protons); 7.20–7.00 (3H, m, aromatic protons).

EXAMPLE 96

4'-t-Butylphenyl 1-amidino-3-piperidinecarboxylate hydrochloride

The same procedure as in Example 93 was followed using 1 g of 1-amidino-3-piperidinecarboxylic acid hydrochloride, 2 g of bis-(p-t-butylphenyl)sulfite, 5 ml of dry dimethylformamide and 1.5 ml of dry pyridine, thereby obtaining 0.9 g (yield: 56%) of 4'-t-butylphenyl 1-amidino-3-piperidinecarboxylate hydrochloride as white powder having a melting point of 178° to 182° C.

IR $\nu_{max}^{KBr}$ cm$^{-1}$: 1750 (C=O).

NMR(CD$_3$OD)$\delta$: 1.34 (9H, s, C(C$\underline{H}_3$)$_3$); 1.60–4.00 (9H, m, piperidine protons); 6.90–7.50 (4H, m, aromatic protons).

This invention now being fully described, it is apparent to those versed in the art that many changes and modifications can be made to the invention without departing the spirit or scope of the invention set forth herein.

What is claimed is:

1. A compound of the following formula or a pharmaceutically acceptable salt thereof,

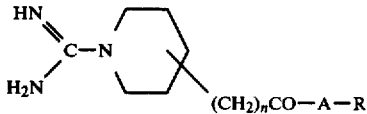

wherein R represents a hydrogen atom, a naphthyl, indanyl, tetrahydronaphthyl or pyridyl group, or a phenyl group which optionally contains 1 to 3 substituents selected from the group consisting of a halogen atom, and a lower alkyl, lower alkenyl, lower alkoxy, lower alkanoyl, cyclohexyl, cyano, formyl, trifluoromethyl, phenyl, phenylloweralkyl, lower alkanoylamino, aminosulfonyl, carboxyl, lower alkoxycarbonyl, benzyloxycarbonyl, benzoylvinyl, phenylvinylcarbonyl, carboxyvinyl, and diphenylmethyloxycarbonylvinyl group, A represents an oxygen or sulfur atom, and n represents an integer of 0 to 3, with the proviso that when n is an integer of 0, R is not a hydrogen atom.

2. A compound of the following formula or a pharmaceutically acceptable salt thereof,

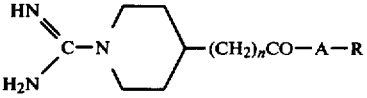

wherein R represents a hydrogen atom, a naphthyl, indanyl, tetrahydronaphthyl or pyridyl group, or a phenyl group which optionally contains 1 to 3 substituents selected from the group consisting of a halogen atom, and a lower alkyl, lower alkenyl, lower alkoxy, lower alkanoyl, cyclohexyl, cyano, formyl, trifluoromethyl, phenyl, phenylloweralkyl, lower alkanoylamino, aminosulfonyl, carboxyl, lower alkoxycarbonyl, benzyloxycarbonyl, benzoylvinyl, phenylvinylcarbonyl, carboxyvinyl, and diphenylmethyloxycarbonylvinyl group, A represents an oxygen or sulfur atom, and n represents an integer of 0 to 3, with the proviso that when n is an integer of 0, R is not a hydrogen atom.

3. A compound of the following formula or a pharmaceutically acceptable salt thereof,

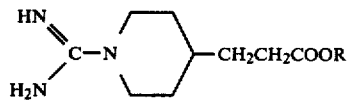

wherein R represents a naphthyl, indanyl, tetrahydronaphthyl or pyridyl group, or a phenyl group which optionally contains 1 to 3 substituents selected from the group consisting of a halogen atom, and a lower alkyl, lower alkenyl, lower alkoxy, lower alkanoyl, cyclohexyl, cyano, formyl, trifluoromethyl, phenyl, phenylloweralkyl, lower alkanoylamino, aminosulfonyl, carboxyl, lower alkoxycarbonyl, benzyloxycarbonyl, benzoylvinyl, phenylvinylcarbonyl, carboxyvinyl, and diphenylmethyloxycarbonylvinyl group.

* * * * *